United States Patent [19]

Ryono et al.

[11] 4,452,791

[45] Jun. 5, 1984

[54] AMINOALKYL AND RELATED SUBSTITUTED PHOSPHINIC ACID ANGIOTENSIN CONVERTING ENZYME INHIBITORS

[75] Inventors: Denis E. Ryono, Princeton; Edward W. Petrillo, Jr., Pennington, both of N.J.

[73] Assignee: E. R. Squibb & Sons, Inc., Princeton, N.J.

[21] Appl. No.: 357,941

[22] Filed: Mar. 15, 1982

[51] Int. Cl.³ .................. A61K 31/675; C07F 9/65
[52] U.S. Cl. ...................... 424/200; 546/22; 546/23; 548/112; 548/119; 548/409; 548/413; 548/414
[58] Field of Search ............... 548/409, 413, 414, 112, 548/119; 546/22, 23; 424/200

[56] References Cited

U.S. PATENT DOCUMENTS

| | | | |
|---|---|---|---|
| 4,053,651 | 10/1976 | Ondetti et al. | 424/319 |
| 4,105,776 | 8/1978 | Ondetti et al. | 424/274 |
| 4,129,566 | 12/1978 | Ondetti et al. | 546/326 |
| 4,151,172 | 4/1979 | Ondetti et al. | 548/413 |
| 4,154,935 | 5/1979 | Ondetti et al. | 546/189 |
| 4,168,267 | 9/1979 | Petrillo, Jr. | 548/413 |
| 4,192,878 | 3/1980 | Ondetti et al. | 424/270 |
| 4,199,512 | 4/1980 | Ondetti et al. | 548/455 |
| 4,217,359 | 8/1980 | Krapcho | 424/274 |
| 4,234,489 | 11/1980 | Ondetti et al. | 424/274 X |
| 4,256,751 | 3/1981 | Hayashi | 424/258 |
| 4,303,583 | 12/1981 | Kim et al. | 424/200 X |
| 4,310,461 | 1/1982 | Krapcho | 546/203 X |
| 4,316,896 | 2/1982 | Thorsett et al. | 548/414 X |
| 4,316,905 | 2/1982 | Krapcho | 424/274 |
| 4,337,201 | 6/1982 | Petrillo, Jr. | 548/413 |
| 4,374,131 | 2/1983 | Petrillo, Jr. | 424/200 |
| 4,379,146 | 4/1983 | Greenlee et al. | 424/177 |
| 4,381,297 | 4/1983 | Karanewsky et al. | 424/200 |

FOREIGN PATENT DOCUMENTS

| | | |
|---|---|---|
| 868532 | 6/1978 | Belgium . |
| 0000833 | 2/1979 | European Pat. Off. ......... 424/200 |
| 9183 | 4/1980 | European Pat. Off. . |
| 2027025 | 2/1980 | United Kingdom . |
| 2028327 | 3/1980 | United Kingdom . |
| 2039478 | 8/1980 | United Kingdom . |
| 2048863 | 12/1980 | United Kingdom . |

Primary Examiner—Donald G. Daus
Assistant Examiner—Diana G. Rivers
Attorney, Agent, or Firm—Lawrence S. Levinson; Burton Rodney

[57] ABSTRACT

Compounds of the structure

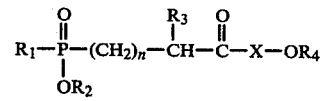

are provided which are inhibitors of angiotensin converting enzyme and are useful in the treatment of hypertension.

17 Claims, No Drawings

AMINOALKYL AND RELATED SUBSTITUTED PHOSPHINIC ACID ANGIOTENSIN CONVERTING ENZYME INHIBITORS

BACKGROUND OF THE INVENTION

Thorsett, et al in European Patent Application Ser. No. 9,183 disclose phosphoryl derivatives of aminoacids including proline. These compounds are disclosed as being hypotensive agents due to their angiotensin converting enzyme inhibition activity.

Petrillo in U.S. Pat. No. 4,168,267 discloses that various phosphinylalkanoyl substituted prolines are useful as hypotensive agents due to their ability to inhibit the angiotensin converting enzyme.

Ondetti, et al in U.S. Pat. No. 4,151,172 discloses that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti et al in U.S. Pat. No. 4,105,776 disclose such compounds wherein the proline ring is unsubstituted or substituted by an alkyl or hydroxy group. Ondetti et al in U.S. Pat. No. 4,154,935 disclose such compounds wherein the proline ring is substituted with one or more halogens. Ondetti et al in U.K. patent application No. 2,028,327 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.K. patent application No. 2,039,478 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti et al in U.S. Pat. No. 4,234,489 disclose such compounds wherein the proline has a keto substituent in the 5-position. Krapcho et al in U.S. Pat. No. 4,310,461 disclose such compounds wherein the proline has an imido, amido, or amino substituent in the 4-position. Iwao, et al in U.K. patent application No. 2,027,025 disclose such compounds wherein the proline has an aromatic substituent in the 5-position. Petrillo in U.S. Pat. No. 4,337,201 discloses various phosphinylalkanoyl substituted prolines. Ondetti et al in U.S. Pat. Nos. 4,053,651 and 4,199,512 disclose that mercaptoacyl derivatives of various aminoacids other than proline are also useful angiotensin converting enzyme inhibitors.

Mercaptoacyl derivatives of 3,4-dehydroproline and disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Pat. No. 868,532.

Mercaptoacyl derivatives of dihydroisoindole carboxylic acids and tetrahydroisoquinoline carboxylic acids are disclosed as being useful hypotensive agents by Ondetti et al in U.S. Ser. No. 69,031 filed Aug. 23, 1979. These mercaptoacyl tetrahydroisoquinoline compounds are also disclosed by Portloch in U.K. Application No. 2,048,863 and by Hayashi et al in U.S. Pat. No. 4,256,751.

DESCRIPTION OF THE INVENTION

This invention is directed to new aminoalkyl and related substituted phosphinic acids of formula I and salts thereof

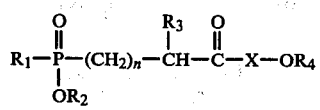

wherein $R_1$ is lower alkyl, aryl, arylalkyl, cycloalkyl, cycloalkylalkyl, furyl, furylalkyl, thienyl, thienylalkyl, pyridyl, pyridylalkyl, aminoalkyl or

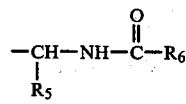

and $R_5$ and $R_6$ are independently selected from hydrogen, lower alkyl, haloalkyl, aryl, alkylaryl, cycloalkyl, cycloalkylalkyl, furyl, furylalkyl, thienyl, thienylalkyl, pyridyl or pyridylalkyl;

$R_2$ and $R_4$ each is independently hydrogen, lower alkyl, arylalkyl, benzhydryl or

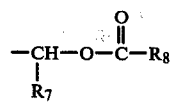

wherein $R_7$ is hydrogen, lower alkyl or phenyl, $R_8$ is hydrogen, lower alkyl, lower alkoxy or phenyl or $R_7$ and $R_8$ taken together are $-(CH_2)_2-$, $-(CH_2)_3-$, $-CH=CH-$, or

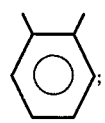

n is 0 or 1;
$R_3$ is $NH_2(CH_2)_m-$,

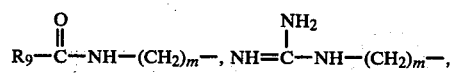

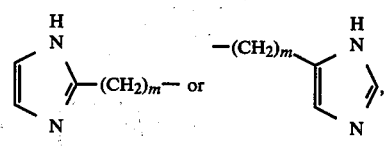

$R_9$ is hydrogen, lower alkyl, aryl or arylalkyl, and m is 0 or an integer of from 1 to 5, and $-XOR_4$ is an amino or amino acid derivative of the formula

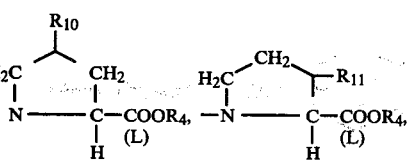

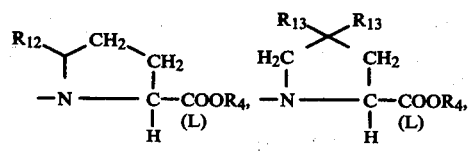
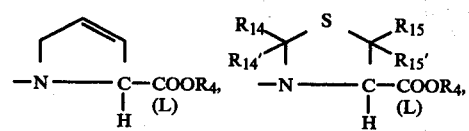
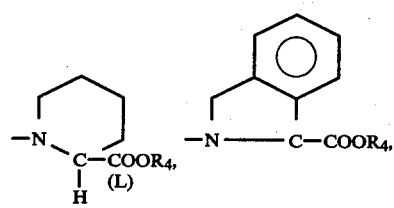
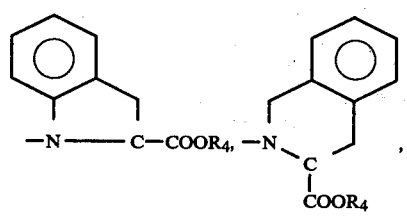
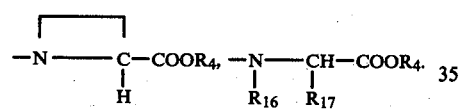
$R_{10}$ is hydrogen, lower alkyl, halogen, keto, hydroxy,
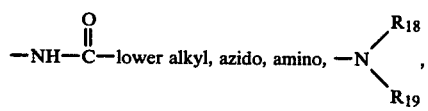
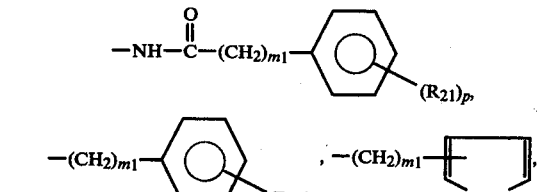
a 1- or 2-naphthyl of the formula
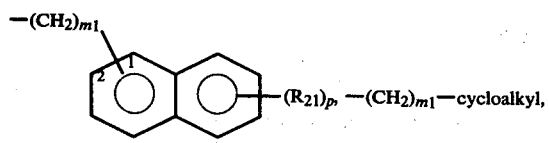
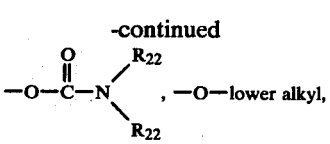, —O—lower alkyl,
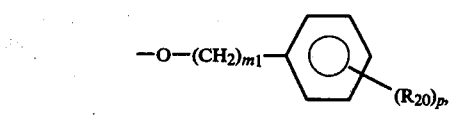
a 1- or 2-naphthyloxy of the formula
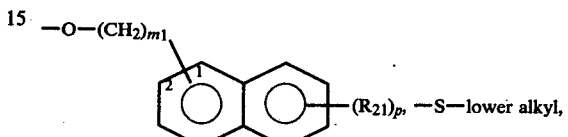, —S—lower alkyl,
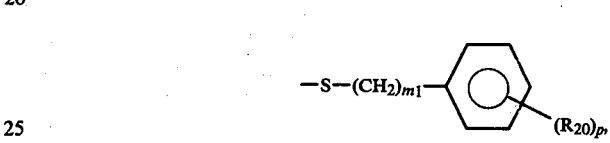
or a 1- or 2-naphthylthio of the formula
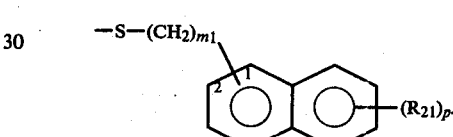
$R_{11}$ is keto, halogen,
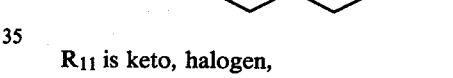,
—O—lower alkyl, a 1- or 2-naphthyloxy of the formula
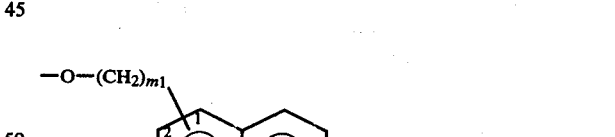
—S—lower alkyl, 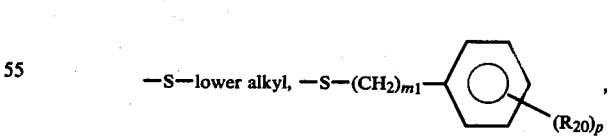,
or a 1- or 2-naphthylthio of the formula
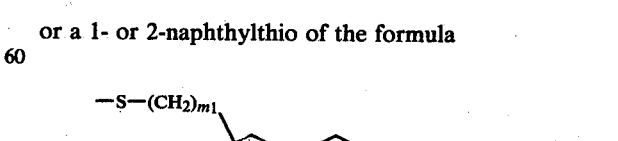
$R_{12}$ is keto or

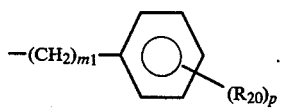

$R_{13}$ is halogen or —Y—$R_{23}$.

$R_{14}$, $R'_{14}$, $R_{15}$ and $R'_{15}$ are independently selected from hydrogen and lower alkyl or $R'_{14}$, $R_{15}$ and $R'_{15}$ are hydrogen and $R_{14}$ is

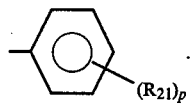

$R_{20}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{21}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

$m_1$ is 0 or an integer from 1 to 5, p is 1, 2 or 3 provided that p is more than 1 only if $R_{20}$ or $R_{21}$ is hydrogen, methyl, methoxy, chloro, or fluoro.

$R_{22}$ is hydrogen or lower alkyl of 1 to 4 carbons.

Y is oxygen or sulphur.

$R_{23}$ is lower alkyl of 1 to 4 carbons,

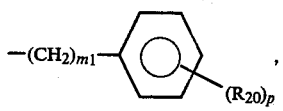

or the $R_{23}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{16}$ is hydrogen, lower alkyl, cycloalkyl, or

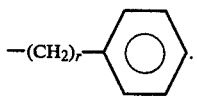

$R_{17}$ is hydrogen, lower alkyl,

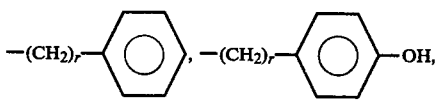

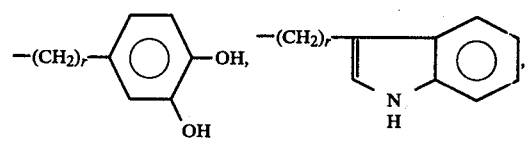

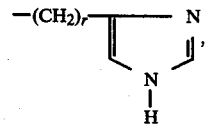

—$(CH_2)_r$—$NH_2$, —$(CH_2)_r$—$SH$, —$(CH_2)_r$—$S$—lower alkyl,

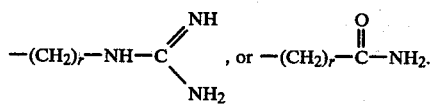

r is an integer from 1 to 4.

$R_{18}$ is lower alkyl, benzyl, or phenethyl.

$R_{19}$ is hydrogen, lower alkyl, benzyl or phenethyl.

Preferred embodiments of this invention are those compounds of formula I wherein n is 0 or 1, $R_1$ is a phenyl or phenylalkyl, especially phenyl-$C_1$–$C_5$ alkyl; $R_2$ is hydrogen,

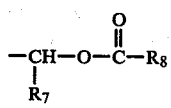

wherein $R_7$ is hydrogen or lower alkyl and $R_8$ is lower alkyl, or $R_2$ represents an alkali metal salt, such as lithium; $R_3$ is aminoalkyl, such as amino-$C_2$–$C_5$-alkyl;

X is L-proline, and $R_4$ is hydrogen, or represents an alkali metal salt.

Other preferred compounds of this invention with respect to the amino or imino acid or ester part of the structure of formula I are those wherein:

$R_{16}$ is hydrogen.

$R_{17}$ is hydrogen, lower alkyl of 1 to 4 carbons,

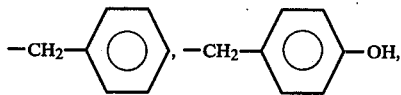

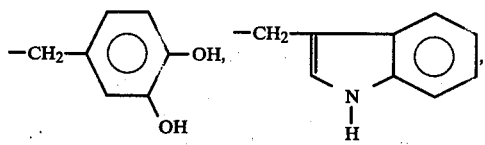

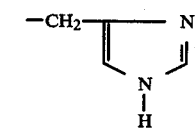

—$(CH_2)_4$—$NH_2$, —$CH_2SH$, —$(CH_2)_2$—$S$—$CH_3$,

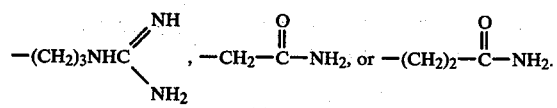

$R_4$ is hydrogen, an alkali metal salt, or

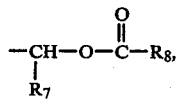

$R_7$ is hydrogen or methyl and $R_8$ is straight or branched chain lower alkyl of 1 to 4 carbons or phenyl.

$R_{10}$ is hydrogen.

$R_{10}$ is hydroxy.

$R_{10}$ is chloro or fluoro.

$R_{10}$ is lower alkyl of 1 to 4 carbons or cyclohexyl.

$R_{10}$ is amino.

$R_{10}$ is —O—lower alkyl wherein lower alkyl is straight or branched chain of 1 to 4 carbons.

$R_{10}$ is

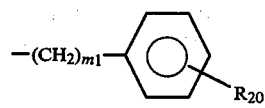

wherein $m_1$ is zero, one or two, $R_{20}$ is hydrogen, methyl, methoxy, methylthio, chloro, bromo, fluoro, or hydroxy.

$R_{10}$ is

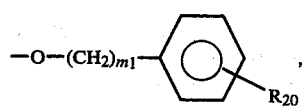

1-naphthyloxy, or 2-naphthyloxy wherein $m_1$ is zero, one or two, and $R_{20}$ is hydrogen, methyl, methoxy, methylthio, chloro, bromo, fluoro, or hydroxy.

$R_{10}$ is —S—lower alkyl wherein lower alkyl is straight or branched chain of 1 to 4 carbons.

$R_{10}$ is

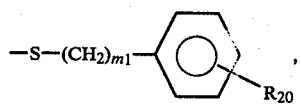

1-naphthylthio, or 2-naphthylthio wherein $m_1$ is zero, one or two, and $R_{20}$ is hydrogen, methyl, methoxy, methylthio, chloro, bromo, fluoro, or hydroxy.

$R_{11}$ is —O—lower alkyl wherein lower alkyl is straight or branched chain of 1 to 4 carbons.

$R_{11}$ is

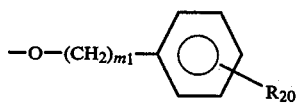

wherein $m_1$ is zero, one or two, and $R_{20}$ is hydrogen, methyl, methoxy, methylthio, chloro, bromo, fluoro, or hydroxy.

$R_{11}$ is —S—lower alkyl wherein lower alkyl is straight or branched chain of 1 to 4 carbons.

$R_{11}$ is

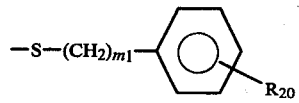

wherein $m_1$ is zero, one or two, and $R_{20}$ is hydrogen, methyl, methoxy, methylthio, chloro, bromo, fluoro, or hydroxy.

$R_{12}$ is phenyl, 2-hydroxyphenyl, or 4-hydroxyphenyl.

$R_{13}$ is both fluoro or chloro.

$R_{13}$ is both —Y—$R_{13}$ wherein Y is O or S, $R_{16}$ is straight or branched chain alkyl of 1 to 4 carbons or the $R_{23}$ groups join to complete an unsubstituted 5- or 6-membered ring or said ring in which one or more of the carbons has a methyl or dimethyl substituent.

$R_{14}$, $R'_{14}$, $R_{15}$ and $R'_{15}$ are all hydrogen, or $R_{11}$ is phenyl, 2-hydroxyphenyl or 4-hydroxyphenyl and $R'_{14}$, $R_{15}$ and $R'_{15}$ are hydrogen.

Most preferred compounds of this invention with respect to the amino or imino acid or ester part of the structure of formula I are those wherein:

X is

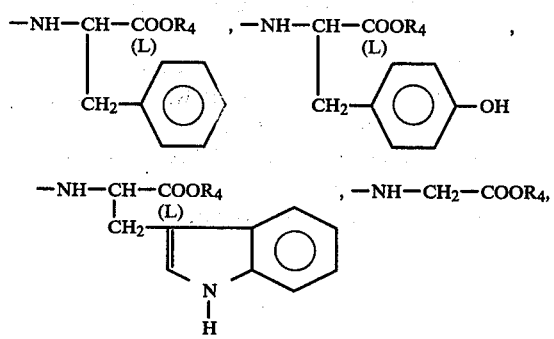

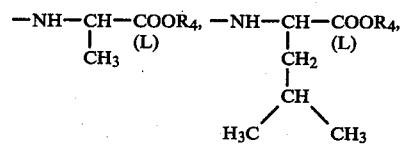

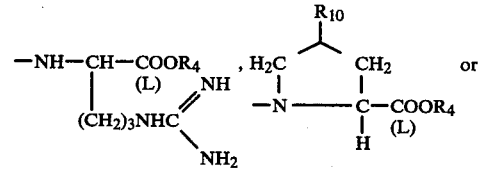

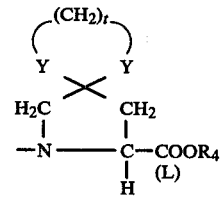

$R_4$ is hydrogen,

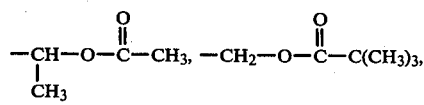

or an alkali metal salt.

R$_{10}$ is hydrogen.

R$_{10}$ is cyclohexyl.

R$_{10}$ is lower alkoxy of 1 to 4 carbons.

R$_{10}$ is

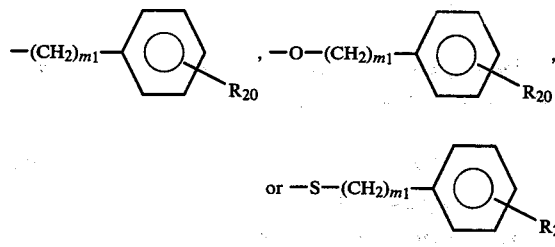

wherein m$_1$ is zero, one, or two and R$_{20}$ is hydrogen, methyl, methoxy, methylthio, Cl, Br, F or hydroxy.

Y is oxygen or sulfur and t is two or three, especially wherein Y is sulfur and t is two.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group refers to straight or branched chain hydrocarbon radicals having up to ten carbons, for example, methyl, ethyl, propyl, isopropyl, butyl, isobutyl, t-butyl, pentyl, isopentyl, heptyl octyl, decyl, etc. The term "lower alkyl" used in defining various symbols refers to straight or branched chain radicals having up to seven carbons. The preferred lower alkyl groups are up to four carbons with methyl and ethyl most preferred.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are fluorine and chlorine.

The term "alkanoyl", as used throughout the specification either by itself or as part of a larger group, refers to alkyl groups as defined above linked to a carbonyl group.

The term "cycloalkyl" as used throughout the specification either by itself or as part of a larger group, refers to saturated rings of 3 to 7 carbon atoms with cyclopentyl and cyclohexyl being most preferred.

The term "halo substituted lower alkyl" refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term "aminosubstituted lower alkyl" refers to lower alkyl groups in which one or more hydrogens have been replaced by —NH$_2$, i.e., aminomethyl, 2-aminoethyl, etc.

The terms furylalkyl

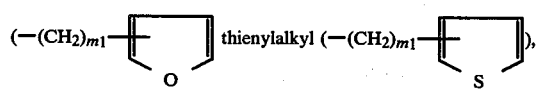

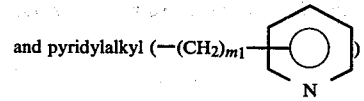

represent that the alkylene bridge is attached to an available carbon atom.

Compounds of formula I wherein n is 0, and R$_3$ is NH$_2$(CH$_2$)$_m$—, that is

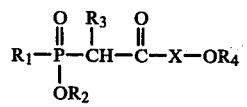

II may be prepared by coupling a phosphinylacetic acid (or its activated form) of the formula III

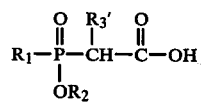

III wherein R$'_3$ represents a protected form of the R$_3$ group, such as, Prot—NH—(CH$_2$)$_m$ with an imino or amino acid or ester of the formula IV

 HX—OR$_4$    IV in the presence of a coupling agent, such as diphenylphosphorylazide, dicyclohexylcarbodiimide, N,N-carbonyldiimidazole and the like, to form

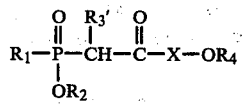

V

Removal of protecting groups where present, such as, by hydrogenation where the protecting group is phenylmethoxycarbonyl or by treatment with hydrazine where the protecting group is phthalidyl affords the formula II compounds of the invention.

Compounds of formula I wherein n is 1, and R$_3$ is NH$_2$(CH$_2$)$_m$—,

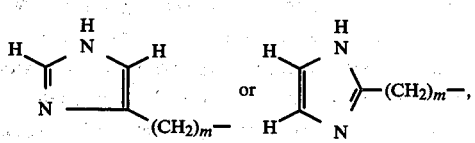

that is

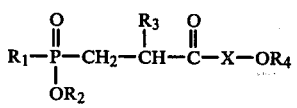

VI may be prepared by treating an acrylate ester $$CH_2=C\diagup^{R_3'}_{COOCH_3} \quad \text{VII}$$

with the requisite phosphonous diester $$R_1-P\diagup^{Olower\ alkyl}_{Olower\ alkyl} \quad \text{VIII}$$

to produce the Michael adduct $$R_1-\underset{OR_2'}{\underset{|}{\overset{O}{\overset{\|}{P}}}}-CH_2-\underset{|}{\overset{R_3'}{\underset{}{CH}}}-COOlower\ alkyl \quad \text{IX}$$

which is then saponified, coupled to amino acid or ester IV to form $$R_1-\underset{OR_2'}{\underset{|}{\overset{O}{\overset{\|}{P}}}}-CH_2-\underset{|}{\overset{R_3'}{CH}}-\overset{O}{\overset{\|}{C}}-X-OR_4. \quad \text{X}$$

Removal of the protecting groups from $R'_2$ and $R'_3$ of compound X affords phosphinic acids VI.

The term "activated form" refers to the conversion of the acid to a mixed anhydride, symmetrical anhydride, acid chloride, or activated ester, see Methoden der Organischen Chemie (Houben-Weyl), Vol. XV, part II, page 1 et seq. (1974) for a review of the methods of acylation. Preferably the reaction is performed in the presence of a coupling agent such as 1,1-carbonyldiimidazole, thionyl chloride, or dicyclohexylcarbodiimide.

Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The products of formula I wherein either or both of $R_2$ and $R_4$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_2$ and $R_4$ are hydrogen.

Compounds of formula I wherein $R_3$ is $$R_9-\overset{O}{\overset{\|}{C}}-NH-(CH_2)_m-,$$

and $R_9$ is other than H, that is, $$\begin{array}{c}R_9-C=O\\|\\NH\\|\\R_1-\underset{OR_2}{\underset{|}{\overset{O}{\overset{\|}{P}}}}-(CH_2)_n-\overset{(CH_2)_m}{\underset{}{CH}}-\overset{O}{\overset{\|}{C}}-X-OR_4\end{array} \quad \text{XI}$$

may be prepared by reacting a compound of formula XII or XIII, that is $$\begin{array}{c}NH_2\\|\\\ \ (CH_2)_m\\R_1-\underset{OR_2}{\underset{|}{\overset{O}{\overset{\|}{P}}}}-\overset{|}{CH}-\overset{O}{\overset{\|}{C}}-X-OR_4\end{array} \quad \text{XII}$$

$$\begin{array}{c}NH_2\\|\\\ \ (CH_2)_m\\R_1-\underset{OR_2}{\underset{|}{\overset{O}{\overset{\|}{P}}}}-CH_2-\overset{|}{CH}-\overset{O}{\overset{\|}{C}}-X-OR_4\end{array} \quad \text{XIII}$$

with an appropriate acid anhydride of the structure $$(R_9\overset{O}{\overset{\|}{C}})_2O \quad \text{XIV}$$

in the presence of a strong base such as sodium hydroxide.

Compounds of formula I wherein $R_3$ is $$\underset{NH}{\underset{|}{NH_2}}\atop{NH=C-NH-(CH_2)_m-},$$

n is 0 or 1, that is, $$\begin{array}{c}NH_2\\|\\NH=C\\|\\NH\\|\\\ \ (CH_2)_m\\R_1-\underset{OR_2}{\underset{|}{\overset{O}{\overset{\|}{P}}}}-(CH_2)_m-\overset{|}{CH}-\overset{O}{\overset{\|}{C}}-X-OR_4\end{array} \quad \text{XV}$$

may be prepared by reacting a compound of formula XII or XIII with methoxyurea hydrochloride in a base medium.

In preparing compounds of formula I wherein $R_3$ is $$\begin{array}{c}H\ \ \ \ N\ \ \ \ H\\ \diagdown\ \ \|\ \ \diagup\\ \ \ \ \ \ \ \ \ \ \ \ \ \ \ \ \\N-\!\!\!-\!\!\!-\!\!\!-(CH_2)_m\\ \ \ \ \ \ \ \ \ \ \ \ \ \ \ \ \ \ \ \ \ \ \ \ \ \ \ \ \ \ \ \ |\end{array},$$

and n is 1, that is

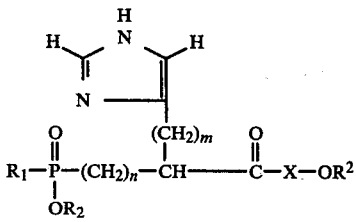

the starting material

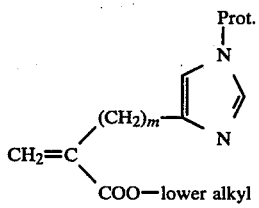

may be prepared by first attaching a protecting group, such as a benzyloxycarbonyl group, on the starting imidazole

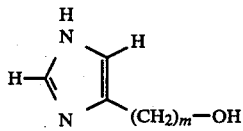

to form the protected compound

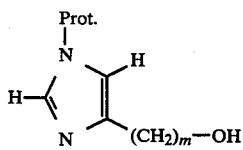

which is then tosylated under an inert atmosphere to form a compound of the structure

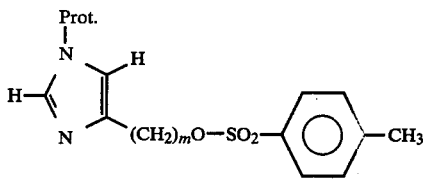

The tosyl derivative XX is then reacted with sodium iodide in the presence of an inert solvent such as acetone to form the corresponding iodide

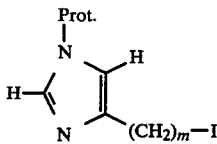

which is used in a later step.

Dimethyl malonate (($CH_3OOC)_2CH_2$) is treated with a base such as sodium hydride in the presence of an inert solvent such as tetrahydrofuran and upon cooling, the cooled reaction mixture is treated with the above previously prepared iodide to form the diester

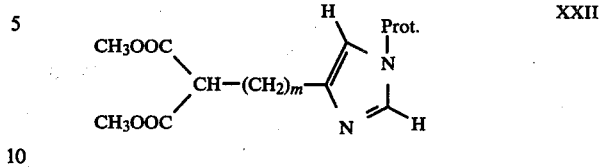

The above diester is then treated with triethylamine in the presence of a dialkylamine salt, such as dimethylamine hydrochloride, dioxane and formalin. The reaction mixture is extracted with ethyl ether and the ether extract is treated with iodomethane to form the alkyliodide salt of the structure

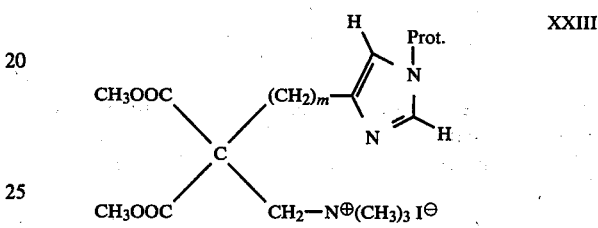

which in turn is heated in the presence of dimethylformamide to form the starting material.

In preparing compounds of formula I wherein $R_3$ is

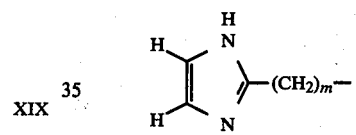

and n is 1, that is,

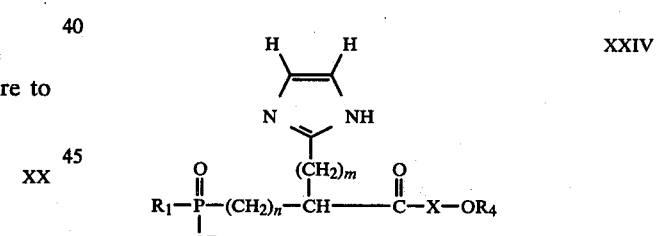

the starting material

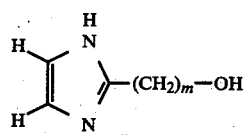

may be prepared by reacting 1-triphenylmethylimidazole

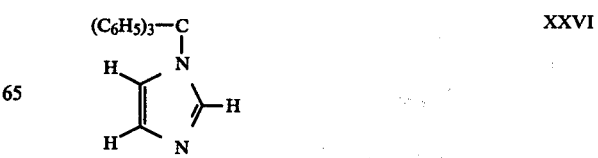

with n-butyl-lithium in an inert solvent such as tetrahydrofuran and after cooling, treating the reaction mixture with an iodotetrahydropyran-2-yloxyalkane of the structure

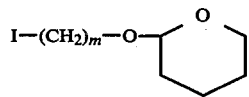   XXVII to form an imidazole compound of the structure

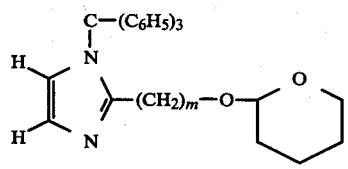   XXVIII which is treated with an organic acid such as acetic acid to form the starting material XXV.

Compounds of formula I wherein n is 0 and $R_3$ is

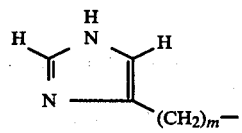

that is

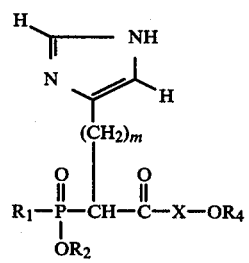   XXIX may be prepared by treating a protected imidazolyl-1-iodo alkane of the structure

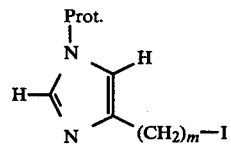   XXI wherein Prot represents a protecting group such as t-butyloxycarbonyl, to remove the protecting group, for example, by treating with trifluoroacetic acid, and anisole, preferably under an inert atmosphere such as nitrogen to form a compound of the structure

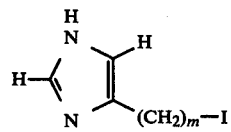   XXX which is used hereinafter.

Phosphinylacetic acid esters having the structure

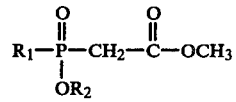   XXXI is treated with a base such as sodium hydride in the presence of an inert solvent such as dimethoxyethane, and preferably under an inert atmosphere, such as argon, and the reaction mixture is then treated with the above imidazolyliodide compound to form a compound of the structure

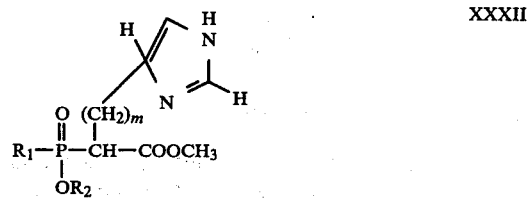   XXXII

The diester XXXII is then treated with an imino or amino acid or ester of formula IV

HX-OR$_4$   IV in the presence of a coupling agent as described hereinbefore to form the compound of the invention

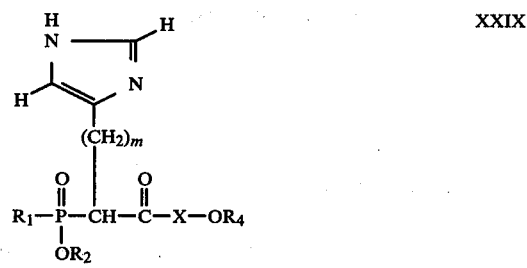   XXIX

Compounds of formula I wherein $R_3$ is

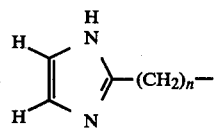

and n is 0, that is

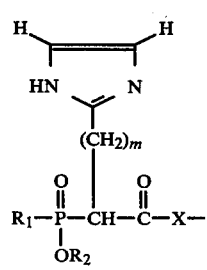   XXIV may be prepared by forming the protected imidazolyl iodoalkane

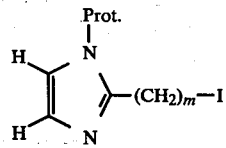

by attaching to the imidazolyl hydroxy alkane

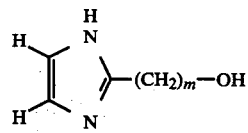

a protecting group, such as a benzyloxycarbonyl group. The protected iodide

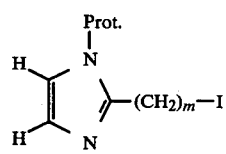

is then employed to form the compounds of the invention as described hereinbefore.

Compounds of formula I wherein $R_3$ is $$H-\overset{O}{\underset{\|}{C}}-NH-(CH_2)_m-$$

and $R_2$ is H and n is 0, that is

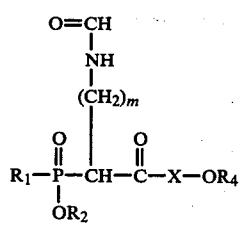

may be prepared by treating a compound of the structure

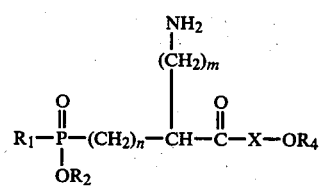

with a mixture of acetic anhydride and formic acid.

The ester products of formula I wherein $R_4$ is

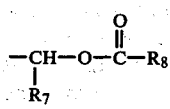

may be obtained by employing the imino or amino acid of formula III or IX in the above reactions with the ester group already in place. Such ester reactants can be prepared by treating imino or amino acids with an acid chloride such as

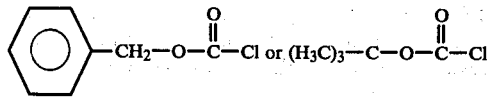

so as to protect the N-atom. The protected acid compound is then reacted in the presence of base with a compound of the formula $$L-\underset{\underset{R_7}{|}}{CH}-O-\overset{O}{\underset{\|}{C}}-R_8 \qquad XI$$

wherein L is a leaving group such as chlorine, bromine, tolylsulfonyloxy, etc., followed by removal of the N-protecting group such as by treatment with acid or hydrogenation.

The ester products of formula I wherein $R_4$ is

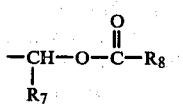

can also be obtained by treating the product of formula I wherein $R_4$ is hydrogen with a molar equivalent of the compound of formula XI. The diester products wherein $R_2$ and $R_4$ are the same and are

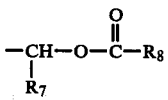

can be obtained by treating the product of formula I wherein $R_2$ and $R_4$ are both hydrogen or an alkali metal salt with two or more equivalents of the compound of formula XI.

The ester products of formula I wherein $R_2$ is

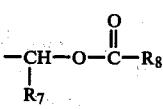

can be obtained by treating the product of formula I wherein $R_2$ is hydrogen or an alkali metal salt and $R_4$ is benzyl or benzhydryl with the compound of formula XI in the presence of base. Removal of the $R_4$ ester group such as by hydrogenation yields the products of formula I wherein $R_2$ is

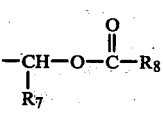

and $R_4$ is hydrogen.

The products of formula I wherein $R_{10}$ is amino may be obtained by reducing the corresponding products of formula I wherein $R_{10}$ is azido.

Compounds of formula I wherein $R_2$ is hydrogen can alternatively be obtained by (i) treating a corresponding compound of formula I wherein $R_2$ is alkyl with a halosilane such as bromotrimethylsilane and then water or (ii) catalytic hydrogenation of a corresponding compound of formula I wherein $R_2$ is benzyl, e.g., using palladium on charcoal. These products have the formula

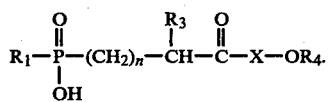

Ia

Compounds of formula I wherein $R_4$ is hydrogen, i.e., compounds having the formula

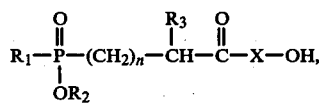

Ib can be obtained by basic hydrolysis of a compound of formula I or Ia. Alternatively, a compound of formula I or Ia wherein $R_4$ is an easily removable ester group (such as t-butyl) can be treated with trifluoroacetic acid and anisole to obtain the carboxylic acids of formula Ib.

The phosphinylalkanoyl substituted prolines of formula I wherein n is 1 can alternatively be prepared by reacting a proline derivative of formula IV with a phospholane having the formula

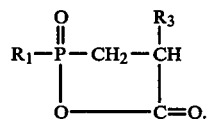

A

The reaction proceeds most readily when run in the presence of an organic base, e.g., triethylamine, pyridine, N,N-dimethylamine or the like, in an inert organic solvent such as acetonitrile, dichloromethane, ether, tetrahydrofuran, or the like.

Phosphinyl-acetic or propionic acid derivatives of formula III can be prepared using known procedures; see, for example, U.S. Pat. No. 4,168,267, issued Sept. 18, 1979. Phospholanes of formula XI can be prepared following the procedures described in Zh. Obsh. Kim., 37:411 (1967) and Zh. Obsh. Kim., 38:288 (1968).

The various imino and amino acids and esters of formula IV are described in the literature and in the various patents and pending U.S. applications referred to above. Various substituted prolines are also disclosed by Mauger et al., Chem. Review, Vol. 66, p. 47–86 (1966).

Ondetti et al disclose various alkyl, halogen, ether and thioether substituted prolines in U.S. Pat. Nos. 4,105,776, 4,154,935, and U.K. Application No. 2,028,327. Iwao et al in U.K. Application No. 2,027,025 disclose various 5-substituted prolines.

When the amino or imino acid is known, it can be readily converted to the ester by conventional means. For example, the esters where $R_4$ is t-butyl can be obtained by treating the corresponding N-carbobenzyloxyimino acid with isobutylene under acidic conditions and then removing the N-carbobenzyloxy protecting group by catalytic hydrogenation and the esters wherein $R_4$ is benzyl can be obtained by treating the imino acid with benzyl alcohol and thionyl chloride.

As disclosed by Krapcho in U.S. Ser. No. 164,985, the substituted prolines wherein

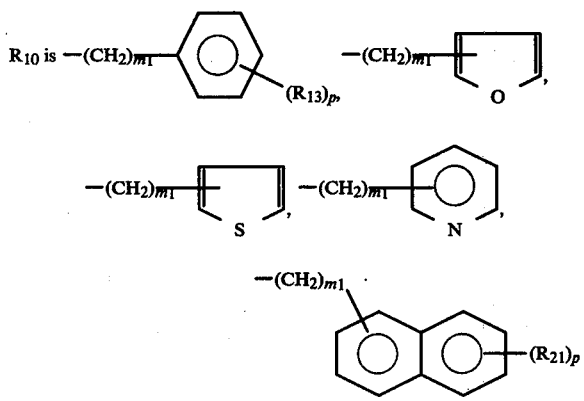

or $-(CH_2)_m-$cycloalkyl are prepared by reacting a 4-keto proline of the formula

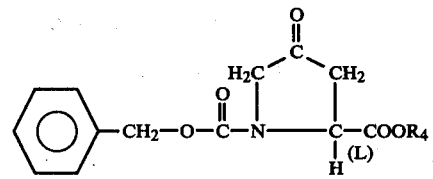

XII with a solution of the Grignard or lithium reagent $R_{10}$-Mg-halo or $R_{10}$-Li  XIII wherein $R_{10}$ is as defined above and halo is Br or Cl to yield

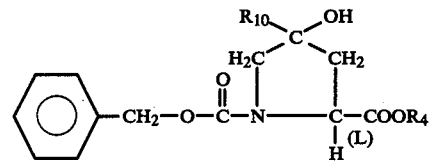

XIV

This compound is treated with a dehydrating agent such as p-toluenesulfonic acid, sulfuric acid, potassium bisulfate, or trifluoroacetic acid to yield the 3,4-dehydro-4-substituted proline of the formula

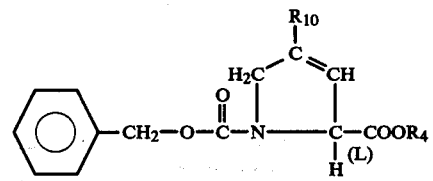

XV

Removal of the N-benzyloxycarbonyl protecting group and hydrogenation of the compound of formula XI yields the desired starting materials. The substituted proline wherein $R_{10}$ is cyclohexyl can be prepared by further hydrogenation of the 4-phenyl proline compound.

The substituted prolines wherein $R_{10}$ is the substituted amino group

may be prepared by reacting a 4-keto proline of formula XII with the amine

in the presence of hydrogen and catalyst or in the presence of sodium cyanotrihydridoborate.

As disclosed by Krapcho in U.S. Ser. No. 66,119, filed Aug. 12, 1979, the carbamoyloxy substituted prolines can be obtained by reacting the hydroxy substituted N-protected proline with phosgene and then a dialkylamine. Removal of the N-protecting group yields the desired starting material.

As disclosed by Krapcho in U.S. Ser. No. 99,164, filed Nov. 30, 1979, the prolines of the formula

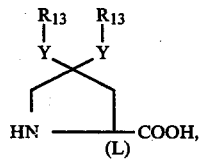  B and esters thereof, can be prepared by reacting a keto compound of the formula

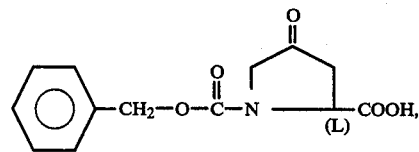  C or ester thereof, with an alcohol or thiol having the formula

  (I)

$R_{13}$-Y-H in the presence of an orthoformate or thioformate of the formula $HC(Y-R_{13})_3$ and an acid such as concentrated sulfuric acid or p-toluenesulfonic acid. Removal of the carbobenzyloxy group by catalytic hydrogenation when Y is oxygen or by treatment with hydrogen bromide and acetic acid when Y is sulfur yields the desired compound.

The formula III starting material may be prepared by alkylating an anion derived from an alkyl or (substituted)aralkylalkoxyphosphinyl acetic acid, alkyl ester, that is

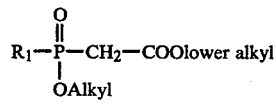  XVI by a primary halide derivative of $R_3$ (e.g., $R_3$-Br) which contains suitable protection for the $R_3$ group, in the presence of a base such as sodium hydride and an inert solvent such as tetrahydrofuran to form

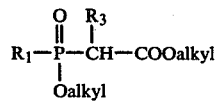  XVII

Saponification of XVII yields the acid III.

The formula VII starting material may be prepared by standard literature procedures.

The compounds of this invention wherein at least one of $R_2$ or $R_4$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product. The salts are formed using conventional techniques.

As shown above, the amino or imino acid or ester portion of the molecule of the products of formula I represented by X is in the L-configuration. Due to the presence of $R_3$, there is at least one other asymmetric center present in the sidechain, and possibly others depending on the definition of $R_2$. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_{10}$, $R_{11}$ and $R_{12}$ substituent in the starting material of the formula III.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a psuedoglobulin in blood pressure, produced angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensin→(renin)-→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg of a compound of this invention, and about 15 to 300 mg, preferably about 15 to 200 mg of the diuretic, to a mammlain species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention and represent preferred embodiments thereof. Temperatures are given in degrees centigrade. AG-50W-X8 refers to a crosslinked polystyrene-divinylbenzene sulfonic acid cation exchange resin. HP-20 refers to a porous crosslinked polystyrene-divinyl benzene polymer resin.

EXAMPLE 1

(±)-1-[5-Amino-2-[hydroxy-(4-phenylbutyl)phosphinyl]-1-oxopentyl]-L-proline

A. 1-Bromo-3-(N-triphenylmethyl)aminopropane

To a mixture of 20 g (91.4 mmol) of 1-bromo-3-aminopropane, hydrobromide (Aldrich) and 18.5 g (183 mmol) of triethylamine in 200 ml of $CH_2Cl_2$ was added 22.9 g (82.3 mmol) of triphenylmethyl chloride (Aldrich). The mixture was kept under nitrogen at room temperature for 48 hours, then diluted with 1.5 liters of ethyl acetate and rinsed with three 500 ml portions of water, brine and dried ($MgSO_4$). The organic solution was concentrated in vacuo to 30 g of crude product from which 15.7 g (m.p. 103°–105° C.) of 1-bromo-3-(N-triphenylmethyl)aminopropane was obtained by crystallization from hot hexanes. Concentration and dilution of the mother liquor with more hexanes afforded 4.2 g (m.p. 98°–101° C.) of a second crop of 1-bromo-3-(N-triphenylmethyl)aminopropane bringing the yield to 16.9 g (64%).

B. [Ethoxy(4-phenylbutyl)phosphinyl]acetic acid, methyl ester (4-Phenylbutyl)phosphonous)acid, diethyl ester, prepared as described in U.S. Pat. No. 4,168,267 (1005 gm, 3.96 mole) was added dropwise to methylbromoacetate (635 gm, 4.15 mole) under an argon atmosphere with ice cooling at such a rate as to maintain the internal temperature between 50°–60° C. When the addition was complete (about 1 hour was required), the mixture was heated at 60° C. (bath temp.) for 1.5 hours, then maintained at 60° C. under vacuum until no more volatiles collected in a dry ice-acetone trap. The product was essentially pure [ethoxy(4-phenylbutyl)phosphinyl]acetic acid, methyl ester.

Anal. Calcd for $C_{12}H_{17}O_4P$: C, 56.24; H, 6.69; P, 12.09; Found: C, 56.11; H, 6.42; P. 12.1.

C. 5-(N-Triphenylmethyl)amino-2-[ethoxy(4-phenylbutyl)phosphinyl]pentanoic acid, methyl ester To a suspension of 89.2 mg (3.72 mmol) of NaH (from a rinsed, 60% dispersion in oil) in 1.6 ml of dry DME cooled in an ice-bath under argon was added 1.01 g (3.38 mol) of the title B phosphinic acid side chain diester transferred with a total of 1.5 ml of DME. Immediate gas evolution was observed and the ice-bath was removed for 15 minutes, at the end of which time a clear yellow-green solution was obtained. The reaction mixture was then treated with 1.93 g (5.08 mmol) of 1-bromo-3-(N-triphenylmethyl)aminopropane (prepared as described in part A) dissolved in 5 ml of DME and the solution was stirred at room temperature under argon for 42 hours, then transferred to a separatory funnel with 80 ml of ether. The organic solution was rinsed with three 20 ml portions of water, brine and dried ($MgSO_4$). Concentration in vacuo yielded 2.6 g of viscous oil which was flash chromatographed on 130 g of EM 9385 silica gel using 5% EtOAc-ether. Pooling of the product containing fractions yielded 1.14 g (56%) of title C product: tlc on silica gel, $R_f=0.25$ with 4:1, ether:EtOAc (UV, PMA).

D. 5-(N-Benzyloxycarbonyl)amino-2-[ethoxy(4-phenylbutyl)phosphinyl]pentanoic acid, methyl ester Trifluoroacetic acid (10 ml) was added over a five minute period to 1.10 g (1.84 mmol) of the title C tritylamine in 20 ml of $CH_2Cl_2$ at room temperature, protected by a $CaCl_2$ drying tube. After 45 minutes, the reaction mixture was diluted with 100 ml of ether and extracted with 40 and 20 ml portions of aqueous 1 N HCl and a final 10 ml of water. The acidic aqueous solutions were concentrated in vacuo to afford 534 mg of colorless, viscous oil. This substance was homogeneous by tlc: $R_f=0.54$; silica gel; 4:1:1, n-BuOH:HOAc:$H_2O$ (PMA and ninhydrin). The above crude amine was dissolved in 7.1 ml of dry pyridine under argon. The ice-bath cooled solution was then treated with 349 mg (2.04 mmol) of benzylchloroformate (Aldrich) and stoppered and refrigerated overnight. The reaction mixture was then diluted with 100 ml of EtOAc and rinsed with three 20 ml portions of 1 N HCl, 20 ml of water, saturated aqueous $NaHCO_3$, water and brine, then dried ($MgSO_4$) and concentrated in vacuo to 489 mg of crude product. Flash chromatography on 35 g of EM 9385 silica gel using 30:1, $CH_2Cl_2$:MeOH gave 436 mg of title D product contaminated with benzyl alcohol. Final purification by preparative layer chromatography (20 cm×20 cm×20 mm; silica gel; 25:1, $CH_2Cl_2$:MeOH) yielded 348 mg (65% overall from title C compound) of title D product: tlc on silca gel, $R_f=0.47$ with 15:1, $CH_2Cl_2$:MeOH (UV, PMA).

E. 5-(N-Benzyloxycrbonyl)amino-2-[ethoxy(4-phenylbutyl)phosphinyl]pentanoic acid To a solution of 338 mg (0.69 mmol) of the title D diester in 3 ml of methanol at room temperature under nitrogen was added 1.73 ml of 1 N aqueous NaOH. The reaction mixture was stirred overnight, then diluted with water and rinsed with ether. The aqueous layer was cooled in an ice-bath and acidified with concentrated HCl to pH 1-2 and extracted with EtOAc. The organic extracts were rinsed with water and brine, dried (MgSO$_4$) and evaporated to give 280 mg of title E acid (85%): tlc on silica gel, R$_f$=0.14 with 12:1, CH$_2$Cl$_2$:MeOH (UV, PMA).

F. 1-[5-(N-Benzyloxycarbonyl)amino-2-[ethoxy(4-phenylbutyl)phosphinyl]-1-oxopentyl]-L-proline, t-butyl ester To a solution of 291 mg (0.612 mmol) of title E acid and 136 mg (0.796 mmol) of L-proline, t-butyl ester in 2 ml of dry THF cooled in an ice-bath under argon was added 185 mg (0.673 mmol) of diphenylphosphoryl azide (Aldrich) followed by 68.1 mg (0.673 mmol) of triethylamine. The reaction mixture was kept cold for 4 hours, then allowed to come to room temperature overnight. The reaction mixture was then diluted with 40 ml of EtOAc and rinsed with 5 ml each of 10% KHSO$_4$, water, saturated NaHCO$_3$ and brine, dried (MgSO$_4$) and concentrated in vacuo to 388 mg of crude product. Purification by preparative layer chromatography (20 cm×20 cm×2 mm; silica gel eluted with 20:1, CH$_2$Cl$_2$:MeOH) yielded 293 mg (74%) of coupled title F product: tlc on silica gel, R$_f$=0.3 with 15:1, CH$_2$Cl$_2$:MeOH (UV, PMA).

G. (±)-1-[5-Amino-2-[(hydroxy-4-phenylbutyl)phosphinyl]-1-oxopentyl]-L-proline

Protected intermediate (title D compound) (285 mg, 0.453 mmol) was twice treated overnight with 2 ml of 4 N HBr/HOAc at room temperature in a stoppered flask. The completion of the reaction was judged by tlc (silica gel; 3:1:1, n-BuOH:HOAc:H$_2$O). The reaction mixture was then repeatedly diluted with water and evaporated to yield the crude HBr salt of the desired product. The salt was next dissolved in water and applied to a 20 ml (28 meqv) AG50W-X2 (H$^+$) polystyrene sulfonic acid ion exchange column packed and initially eluted with water to remove HBr. Final elution with 2% aqueous pyridine gave the product as a white solid after lyophilization. The yield of product was 174 mg (91%) as a 0.6 H$_2$O solvate.

EXAMPLE 2

(±)-1-[6-Amino-2-[[hydroxy(4-phenylbutyl)phosphinyl]methyl]-1-oxohexyl]-L-proline, dilithium salt A. 4-Phthalimido-1-iodobutane A solution of 10 g (35.4 mmol) of 4-phthalimido-1-bromobutane (Aldrich) in 160 ml of dry acetone was treated with 53 g (354 mmol) of sodium iodide. After stirring overnight at room temperature, the reaction mixture was filtered, concentrated in vacuo and dissolved in a mixture of 1 l. of ether and 300 ml of ethyl acetate. The organic solution was rinsed with 150 ml portions of H$_2$O, 5% aqueous NaHSO$_3$, H$_2$O and brine, dried (MgSO$_4$) and evaporated to leave 11.4 g (98%) of the title iodide in the form of a white solid iodide. A sample recrystallized from hot ethyl acetate/hexanes had m.p. 85°-87° C. and microanalysis:

Anal. Calcd for C$_{12}$H$_{12}$NO$_2$I: C, 43.79, H, 3.68; N, 4.26; I, 38.56; Found: C, 44.05; H, 3.62; N, 4.22; I, 38.48.

B. 2-Methoxycarbonyl-6-phthalimidohexanoic acid, methyl ester

Neat dimethyl malonate (11 g, 83.2 mmol, Aldrich) was added to an ice-bath cooled suspension of 1.81 g (75.4 mmol) of sodium hydride (from 3.62 g of unwashed 50% dispersion in oil) in 220 ml of dry THF under argon. Upon completion of addition, a clear solution resulted and the cooling bath was removed for 15 minutes, then replaced, and a solution of 24.8 g (75.4 mmol) of title A iodide in 210 ml of dry THF was added over a period of 10 minutes. The reaction mixture was then warmed and refluxed for 9 hours. The reaction was next cooled to room temperature, diluted with 500 ml of ether and rinsed with 100 ml of H$_2$O, two 100 ml portions of 5% aq. NaHSO$_3$, H$_2$O and brine, dried (MgSO$_4$) and evaporated to afford 24.8 g (99%) of crude title B product which was used as such in the next step. This crude product was characterized by $^{13}$C-NMR and TLC (R$_f$=0.64, 0.51 for minor by-product; silica gel using 1:1, EtOAc:hexane; UV, PMA). A sample purified in 75% yield by flash chromatography on EM 9385 silica gel eluted with 50:1, CH$_2$Cl$_2$:EtOAc gave the title product in the form of a solid: m.p. 55°-58° C.

Anal. Calcd for C$_{17}$H$_{19}$NO$_6$: C, 61.25; H, 5.75; N, 4.20; Found: C, 61.28; H, 5.83; N, 4.13.

C. 2-Dimethylaminomethyl-2-methoxycarbonyl-6-phthalimidohexanoic acid, methyl ester, methiodide salt To a mixture of the title B diester (crude product, 24.8 g, nom. 74.4 mmol), dimethylamine hydrochloride (12.8 g, 152 mmol; Aldrich) and 10 ml of formalin (formaldehyde; 3.7 g, 123 mmol) in 30 ml of dioxane was added triethylamine (7.7 g, 76.1 mmol). The mixture was stoppered and stirred at room temperature for 41 hours. The reaction was then treated with 11 ml of triethylamine and treated with 400 ml of ether and 50 ml of water. The ethereal extract was rinsed with more water and brine, dried (Na$_2$SO$_4$) and concentrated in vacuo to 29.2 g of a mixture of mainly product plus some starting material, as characterized by $^{13}$C-NMR. This mixture was used without purification in the next step.

The mixture of title B diester and the desired Mannich base product was dissolved in 30 ml of ether and treated with 52.8 g (372 mmol) of iodomethane. The mixture was stoppered and stirred for 19 hours at room temperature. Filtration and concentration of the mother liquor followed by retreating of the concentrate with 15 ml of iodomethane for 5 hours gave a total of 21.1 g (53% overall yield from dimethyl malonate) of title C methiodide salt: mp 184°-187° C.(d).

Anal. Calcd for C$_{21}$H$_{29}$N$_2$O$_6$I: C, 47.38, H, 5.49; N, 5.26; I, 23.84; Found: C, 47.66; H, 5.37; N, 5.31; I, 23.69.

D. 2-Methylidene-6-phthalimidohexanoic acid, methyl ester

Title C methiodide salt (20.5 g, 38.5 mmol) was heated at 75° C. in 80 ml of dry DMF under argon for 40 hours. At the end of this time, the cooled reaction mixture was filtered with ethyl acetate rinses and concentrated in vacuo to remove DMF. The residue was partitioned between 250 ml of H$_2$O and 150 ml of ether. The aqueous was extracted twice with two more 150 ml portions of ether. The combined ethereal extracts were rinsed with two portions each of 125 ml of H$_2$O, 125 ml of 5% aqueous NaHSO$_3$ and 125 ml of H$_2$O. The extract was then rinsed with brine and dried (MgSO$_4$). Concentration in vacuo yielded 8.87 g of crude product. Flash chromatography on 440 g of silica gel (Whatman LPS-1 and EM 9385) eluted with 3:1, hexane:EtOAc afforded 7.90 g (71%) of title D acrylate as a colorless oil: TLC R$_f$=0.27 on silica gel in 3:1, hexane:EtOAc (UV, PMA).

E. 6-Phthalimido-2-[[ethoxy (4-phenylbutyl)phosphinyl]methyl]-hexanoic acid, methyl ester A mixture of title D acrylate (3.87 g, 13.5 mmol), (4-phenylbutyl)phosphonous acid diethyl ester (4.11 g, 16.2 mmol) and acetic acid (glacial; 1.22 g, 20.2 mmol) was heated at 70° C. under nitrogen for 24 hours. The reaction mixture was then cooled and treated with 1 ml of water, dissolved in 500 ml of ether and rinsed with brine. The organic solution was then dried (MgSO$_4$) and concentrated in vacuo to 7.6 g of crude product. Flash chromatography on 320 g of EM 9385 silica gel eluted sequentially with 1.8 l. of 5:1, ether:hexane, 1 l. of ether, 1.5 l. of 4:1, ether:acetone, 1.6 l. of 3:1, ether:acetone and 1 l. of EtOAc yielded 4.11 g (59%) of essentially pure title E product: TLC R$_f$=0.34, 0.53 (impurity) on silica gel in 4:1, ether:acetone (UV, PMA). A pure sample of the impurity was obtained from earlier fractions and was identified by $^{13}$C-NMR to be phenylbutylphosphonic acid, diethyl ester.

F. 6-Amino-2-[[hydroxy(4-phenylbutyl)phosphinyl]methyl]hexanoic acid

Title E compound (4.11 g, nom. 8 mmol) was refluxed for 20 hours in a mixture of 8 ml each of acetic acid and concentrated HCl and 4 ml of H$_2$O. At the end of this time the cooled reaction mixture was diluted with 200 ml of H$_2$O and rinsed with three 40 ml portions of ether. The aqueous solution was concentrated in vacuo and applied to 120 ml of AG50W-X2 (H+) resin prepared in H$_2$O. After elution of acidic materials, the column was eluted with 2% aqueous pyridine and the resulting ninhydrin positive fractions were pooled to afford after evaporating with H$_2$O and lyophilization 1.82 g (67%) of white powdery title F compound: m.p. 193°–196° C. (d); electrophoresis, +5.3 cm at pH 6.5 (45 min, 2000 V, 55 mA) visualized with ninhydrin and carboxyl spray; satisfactory $^1$H and $^{13}$C-NMR spectra were obtained of the 2Na+-salt.

Anal Calcd for C$_{17}$H$_{28}$NO$_4$P.1.3H$_2$O: C, 58.88; H, 8.31; N, 4.04; P, 8.9; Found: C, 58.83; H, 8.31; N, 4.12; P, 8.8

G. 6-Benzyloxycarbonylamino-2-[[hydroxy(4-phenylbutyl)phosphinyl]methyl]hexanoic acid A stirred suspension of title F aminodiacid (1.64 g, 4.80 mmol) in 7 ml of dry CH$_3$CN under argon at room temperature was treated with 4.94 g (19.2 mmol) of bis-trimethylsilyltrifluoroacetamide. After 90 minutes, benzylcholoroformate (1.23 g, 7.2 mmol) was added. The reaction was stoppered and kept at room temperature for 36 hours, then quenched with 3 ml of water, diluted with 150 ml of saturated NaHCO$_3$ and rinsed with three 40 ml portions of ether. The combined ethereal extracts were back-extracted with 50 ml of saturated NaHCO$_3$. The combined aqueous NaHCO$_3$ solutions were acidified to pH 1–2 with concentrated HCl and extracted with three 150 ml portions of 5:1, EtOAc:ether. The organic solutions were rinsed with two 50 ml portions of water, brine, dried (MgSO$_4$) and concentrated in vacuo to 2.34 g (quantitative) of essentially TLC homogeneous product. Flash chromatogrphy on 33 g of Whatman LPS-1 silica gel using 25:1:1, CH$_2$Cl$_2$:MeOH:HOAc afforded 1.10 g of product from B 1.14 g applied (99% yield): TLC R$_f$=0.13 on silica gel in 20:1:1, CH$_2$Cl$_2$:MeOH:HOAc (UV, PMA).

H. (±)-1-[6-Benzyloxycarbonylamino-2-[[hydroxy(4-phenylbutyl)phosphinyl]methyl]-1-oxohexyl]-L-proline, benzyl ester A solution of 1.20 g (2.52 mmol) of the title G diacid in 7 ml of dry THF under argon was cooled in an ice water bath and treated with 409 mg (2.52 mmol) of carbonyldiimidazole. After 1 hour, L-proline, benzyl ester hydrochloride (609 mg, 2.52 mmol) was added followed by 510 mg (5.04 mmol) of triethylamine. The reaction mixture was allowed to come to room temperature overnight, then treated with 100 ml of EtOAc and rinsed with 15 ml of 10% KHSO$_4$, H$_2$O, brine and dried (MgSO$_4$). Removal of solvents in vacuo yielded 1.7 g of crude product. Flash chromatography on 68 g of LPS-1 Whatman silica gel using 30:1:1, CH$_2$Cl$_2$:MeOH:HOAc afforded 1.21 g (72%) of a mixture of the title H diastereomeric products: TLC R$_f$=0.41, 0.49 on silica gel in 20:1:1, CH$_2$Cl$_2$:MeOH:HOAc (UV, PMA).

I. (±)-1-[6-Amino-2-[[hydroxy(4-phenylbutyl)phosphinyl]methyl]-1-oxohexyl]-L-proline, dilithium salt A solution of 1.21 g (1.82 mmol) of the product of part H in 300 ml of MeOH was treated with a slow flow of H$_2$ at 1 atmosphere at room temperature in the presence of 500 mg of 10% Pd-C. After 7 hours, the reaction mixture was filtered and concentrated to 740 mg of glassy solid. This substance was dissolved in water containing 142 mg (1.69 mmol) of NaHCO$_3$ and passed through a 40 ml column of AG50W-X8 (Li+) resin. Pooling of the ninhydrin positive fractions gave 820 mg of di-Li+ salt. Final purification was achieved on a 25×250 mm Diaion ® reverse-phase polystyrene column using a gradient from 500 ml of H$_2$O to 500 ml of CH$_3$CN taking fractions at 7 ml/2.5 min. Lyophilization of the product containing fractions yielded 620 mg (71%) of the title product as a 1.7.H$_2$O solvate.

EXAMPLE 3

(±)-1-[6-Amino-2-[[[2,2-dimethyl-1-oxopropoxy)methoxy](4-phenylbutyl)phosphinyl]methyl]-1-oxohexyl]-L-proline A. (±)-1-[6-Amino-2-[[[2,2-dimethyl-1-oxopropoxy)methoxy](4-phenylbutyl)phosphinyl]methyl]-1-oxohexyl]-L-proline, benzyl ester To a mixture of 0.435 g (0.656 mmol) of (±)-6-amino-2-[[hydroxy(4-phenylbutyl)phosphinyl]methyl]-1-oxohexyl]-L-proline, dilithium salt and 0.395 g (2.62 mmol) of chloromethyl pivalate (Aldrich) in 0.6 ml of dry DMF was added 0.133 g (1.31 mmol) of triethylamine. The reaction mixture was stoppered under argon and stirred at room temperature for 18 hours, then diluted with ethyl acetate and rinsed with 10% KHSO$_4$, H$_2$O and brine, dried (MgSO$_4$), and concentrated in vacuo to 0.580 g of crude product. Flash chromatography on 50 g of Whatman LPS-1 silica gel using 40:2:1, ether:ethyl acetate:methanol afforded 0.330 g (65%) of the title compound as an oil: TLC R$_f$=0.33 on silica gel in 40:2:1, ether:ethyl acetate:methanol (UV,PMA); [α]$_D$ −39.6° (c=1, CHCl$_3$); satisfactory $^{13}$C and H-NMR and IR spectra were obtained.

B. (±)-1-[6-Amino-2-[[[2,2-dimethyl-1-oxopropoxy)methoxy](4-phenylbutyl)phosphinyl]methyl]-1-oxohexyl]-L -proline To a solution of 0.279 g (0.359 mmol) of the intermediate of title A in a mixture of 8 ml of methanol and 2 ml of acetic acid was added 200 mg of 10% Pd-C. The reaction mixture was subjected to a slow flow of H$_2$ for 5 hours, then flushed with argon and filtered over Celite. The residue after evaporation of solvents was purified by a linear gradient elution from 500 ml of H$_2$O to 500 ml of acetonitrile on a 25×250 mm HP-20 reverse phase column. The product containing fractions were pooled and lyophilized to yield a glassy lyophilizate which was dissolved in 5 ml of H$_2$O and distributed into vials and re-lyophilized to afford a total of 0.144 g (69%) of the title product as 1.6.H₂O solvate.

EXAMPLE 4

(±)-1-[6-Acetylamino-2-[[[hydroxy(4-phenylbutyl)-phosphinyl]methyl]-1-oxohexyl]-L-proline A solution of 3.54 g (7.86 mmol) of (±)-6-amino-2-[[hydroxy-(4-phenylbutyl)phosphinyl]methyl]-1-oxohexyl]-L-proline, dilithium salt prepared as described in Example 2 in 10 ml of water is adjusted to pH 8.5 and cooled in an ice-bath. To this solution is added 1.5 ml of acetic anhydride and 20 ml of 1 N NaOH separately in 10 portions each over a period of 30 minutes. The reaction is allowed to warm to room temperature and is stirred for 2 hours, then acidified with concentrated HCl and extracted with ethyl acetate. The organic solution is rinsed with H₂O and brine, then dried (MgSO₄) and evaporated to yield the title acetylated product.

EXAMPLE 5

(±)-1-[6-Guanidion-2-[[[hydroxy(4-phenylbutyl)phosphinyl]methyl]-1-oxohexyl]-L-proline The guanidino butyl side chain analog of the product of Example 2 may be prepared in a single step from the Example 2 product itself by following the procedure of Beatty and Magrath (I. M. Beatty and David I. Magrath, *J. Am. Chem. Soc.*, 1960. 82, 4983).

A solution of 6.43 g (14.3 mmol) of (±)-6-amino-2-[[hydroxy(4-phenylbutyl)phosphinyl]methyl]-1-oxohexyl]-L-proline, dilithium salt in 16 ml of water is treated with 1.6 g (1 equivalent) of O-methyl-urea hydrochloride (for preparation, see F. Kurzer and A. Lawson, *Org. Syn.*, 1954, 34, 67). The pH of the solution is adjusted to between 10 and 11 by adding 2 N aq. NaOH solution, and the reaction mixture is stoppered and left at room temperature for several days with periodic readjustment of the pH when necessary. The aqueous reaction mixture is then concentrated and chromatographed by reverse-phase chromatography on a Diaion ® HP-20 (Mitsubishi Chemicals) column which is gradient eluted from H₂O to 100% acetonitrile. The product containing fractions are detected by a positive reaction to Sakaguchi reagent spot testing, pooled and lyophilized to yield the title compound.

EXAMPLE 6

(±)-1-[5-(1H-Imidazol-4-yl)-2-[[hydroxy(4-phenylbutyl)phosphinyl]methyl]-1-oxopentyl]-L-proline A. 3-(1-t-Butyloxycarbonylimidazol-4-yl)propane-1-ol A solution of 4.47 g (35.5 mmol) of 3-(1H-imidazol-4-yl)propane-1-ol (prepared according to the procedure described by Kivits et al, *J. Heterocyclic Chem.* 12, 577 (1975)) and 7.03 g (69.5 mmol) of triethylamine in 35 ml of H₂O was treated with 10.9 g (44.2 mmol) of 2-(tert-butoxycarbonyloxyiminol)-2-phenylacetonitrile (Aldrich) dissolved in 35 ml of dioxane. After stirring overnight at room temperature under argon, the reaction mixture is diluted with 10% aqueous KHSO₄ and extracted with ethyl acetate. The combined organic extracts are rinsed with H₂O, saturated NaHCO₃ and brine, then dried (MgSO₄) and concentrated in vacuo to afford the title A compound.

B. 3-(1-t-Butyloxycarbonylimidazol-4-yl)propane-1-p-toluenesulfonate

A solution of 3 g (13.3 mmol) of the compound prepared in part A in 10 ml of dry pyridine is cooled in an ice-bath under a nitrogen atmosphere and heated with 3.80 g (19.9 mmol) of p-toluenesulfonyl chloride. The stoppered reaction mixture is kept in a refrigerator for 3 days, then poured onto ice-water and the product is extracted with portions of ethyl acetate. The combined organic extracts are rinsed with H₂O and brine, dried (MgSO₄) and the solvent removed in vacuo to afford the title B compound.

C. 3-(1-t-Butyloxycarbonylimidazol-4-yl)-1-iodopropane

A solution of 4 g (10.5 mmol) of the compound prepared in part B in 20 ml of dry acetone is treated with 15.7 g (105 mmol) of solid sodium iodide. The reaction mixture is refluxed under a nitrogen atmosphere for 24 hours, then cooled and the reaction mixture partitioned between H₂O and ethyl acetate. The ethyl acetate extract is rinsed with H₂O and 5% aqueous NaHSO₃, then H₂O and finally brine. Removal of solvents in vacuo yields the title C compound.

D. 5-(1-t-Butyloxycarbonylimidazol-4-yl)-2-methoxycarbonylpentanoic acid, methyl ester In the manner described in Example 2, part B, and using 3-(1-t-butoxycarbonylimidazol-4-yl)iodopropane (prepared as described in part C) in place of 4-phthalimido-1-iodobutane, the title D compound is obtained.

E. 2-Dimethylaminomethyl-5-(1-t-butyloxycarbonylimidazol-4-yl)-2-methoxycarbonylpentanoic acid, methyl ester, methiodide salt In the manner described in Example 2, part C, and using 5-(1-t-butyloxycarbonylimidazol-4-yl)-2-methoxycarbonylpentanoic acid, methyl ester in place of 2-methoxycarbonyl-6-phthalimidohexanoic acid, methyl ester, the title E compound is obtained.

F. 5-(1-t-Butyloxycarbonylimidazol-4-yl)-2-methylidenepentanoic acid, methyl ester In the manner described in Example 2, part D, and using 2-dimethylaminomethyl-5-(1-t-butyloxycarbonylimidazol-4-yl)-2-methoxycarbonylpentanoic acid, methyl ester, methiodide salt in place of 2-dimethylaminomethyl-2-methoxycarbonyl-6-phthalimidohexanoic acid, methyl ester, methiodide salt, the title F compound is obtained.

G. 5-(1-t-Butyloxycarbonylimidazol-4-yl)-2-[[ethoxy(4-phenylbutyl)phosphinyl]methyl]pentanoic acid, methyl ester In the manner described in Example 2, part E, and using 5-(1-t-butyloxycarbonylimidazol-4-yl)-2-methylidenepentanoic acid, methyl ester in place of 2-methylidene-6-phthalimidohexanoic acid, methyl ester, the title G compound is obtained.

H. 5-(1-t-Butyloxycarbonylimidazol-4-yl)-2-[[ethoxy(4-phenylbutyl)phosphinyl]methyl]pentanoic acid A solution of 521 mg (1 mmol) of the title G compound in 1 ml of THF is cooled in an ice-bath and treated with 1.2 ml of 1 N aqueous NaOH. After several hours, the reaction mixture is acidified with concentrated HCl and extracted with portions of ethyl acetate. Combined organic extracts are dried (MgSO₄) and evaporated to afford the title H compound.

I. (±)-1-[5-(1-t-Butyloxycarbonylimidazol-4-yl)-2-[[[ethoxy(4-phenylbutyl)phosphinyl]methyl]-1-oxopentyl]-L-proline, t-butyl ester A solution of 506 mg (1 mmol) of the title H compound in 5 ml of dry THF is cooled in an ice-bath under argon and treated with 178 mg (1.1 mmol) of carbonyldimidazole. After 1 hour the reaction is treated with 188 mg (1.1 mmol) of L-proline, t-butyl ester followed by 101 mg (1 mmol) of triethylamine. The reaction mixture is allowed to warm to room temperature, then partitioned between 10% $KHSO_4$ and ethyl acetate. The organic layer is rinsed with $H_2O$, saturated $NaHCO_3$ and brine, then dried ($MgSO_4$) and concentrated in vacuo to yield the title I compound.

J. (±)-1-[5-(1H-Imidazol-4-yl)-2-[[[hydroxy(4-phenylbutyl)phosphinyl]methyl]-1-oxopentyl]-L-proline A solution of 659 mg (1 mmol) of the title I compound in 1 ml of $CH_2Cl_2$ is treated with 214 mg (1.4 mmol) of trimethylsilylbromide. After 4 hours, the reaction mixture is concentrated in vacuo, and redissolved in 4 ml of trifluoroacetic acid containing 0.3 ml of anisole. The reaction mixture is stirred at room temperature for 2 hours, then concentrated in vacuo to remove excess trifluoroacetic acid. The residue is then dissolved in water and chromatographed by reverse phase gradient elution on a Diaion ®HP-20 (Mitsubishi Chemicals) column eluted with water in a linear gradient to acetonitrile. The product containing fractions are detected by a positive Pauly reagent spot test, then pooled and lyophilized to afford the title product.

EXAMPLE 7

(±)-1-[5-(1H-Imidazol-2-yl)-[[[hydroxy(4-phenylbutyl)phosphinyl]methyl]-1-oxopentyl]]-L-proline A. 3-(1-Triphenylmethylimidazol-2-yl)-1-(tetrahydropyran-2-yloxy)propane A solution of 310 mg (1 mmol) of 1-triphenylmethylimidazole (K H. Büchel et al.; *Drugs Made in Germany*, 1972, 15, 77) in 12 ml of dry THF is cooled to 0° under nitrogen and treated with 0.647 ml (1.1 mmol) of 1.7 M solution of n-BuLi in hexane. The solution is stirred at room temperature for 1 hour, then recooled to 0° and treated with 405 mg (1.5 mmol) of 1-iodo-3-(tetrahydropyran-2-yloxy)propane dissolved in 2 ml of dry THF. The reaction mixture is allowed to warm to room temperature overnight, then poured into water and extracted with ethyl acetate. The organic extract is rinsed with brine and dried ($MgSO_4$). Removal of solvents in vacuo affords the title A compound.

B. 1-Hydroxy-3-(1H-imidazol-2-yl)propane

A solution of 452 mg (1 mmol) of the title A compound in 2 ml of THF is treated with 2 ml of acetic acid and 2 ml of 1 N HCl and stirred at room temperature overnight. The reaction mixture is adjusted to pH 11 and extracted with $CHCl_3$. The organic extract is dried ($MgSO_4$) and evaporated to yield the title B compound.

C. (±)-1-[5-(1H-Imidazol-2-yl)-2-[[[hydroxy(4-phenylbutyl)phosphinyl]methyl]-1-oxopentyl]-L-proline In the manner described in Example 6, parts A to J, but by initially substituting 1-hydroxy-3-(1H-imidazol-2-yl)propane for 3-(1H-imidazol-4-yl)propane-1-ol, the title C product is obtained.

EXAMPLE 8

(±)-1-[5-(1H-Imidazol-4-yl)-2-[hydroxy(4-phenylbutyl)phosphinyl]-1-oxopentyl]-L-proline A. 3-(1H-Imidazol-4-yl)-1-iodopropane A solution of 5 g (14.2 mmol) of 3-(1-t-butyloxycarbonylimidazol-4-yl)-1-iodopropane (prepared as described in Example 6, part C) is stirred in a mixture of 5 ml of trifluoroacetic acid, 5 ml of $CH_2CH_2$ and 1 ml of anisole at 0° C. under nitrogen for 6 hours, then concentrated in vacuo and partitioned between $CHCl_3$ and 15% aq $Na_2CO_3$. Evaporation of the organic extracts affords the title A compound.

B. 5-(1H-Imidazol-4-yl)-2-[ethoxy(4-phenylbutyl)phosphinyl]pentanoic acid, methyl ester In the manner described in Example 1, part C, except substituting 3-(1H-imidazol-4-yl)-1-iodopropane for 3-(N-triphenylmethyl)amino-1-bromopropane, the title B compound is obtained.

C. (±)-1-[5-(1H-Imidazol-4-yl)-2-[ethoxy(4-phenylbutyl)phosphinyl]-1-oxopentyl]-L-proline, methyl ester A solution of 3 g (7.39 mmol) of the title B compound in 70 ml of dimethylformamide cooled in an ice bath is treated with 3.65 ml of 2 N aq NaOH. After 4 hours, the reaction mixture is treated with 2.02 g (7.39 mmol) of diphenylphosphoryl azide (Aldrich), triethylamine (0.748 g, 7.39 mmol) and L-proline, methyl ester, hydrochloride (1.22 g, 7.39 mmol). After stirring cold for 3 hours, then at room temperature for 16 hours, the reaction mixture is concentrated in vacuo and partitioned between water and ethyl acetate. Work-up of the organic extract gives the title C compound.

D. (±)-1-[5-(1H-Imidazol-4-yl)-2-[hydroxy(4-phenylbutyl)phosphinyl]-1-oxopentyl]-L-proline A solution of 1 g (1.99 mmol) of the title C compound in 10 ml of $CH_2Cl_2$ is treated with 0.457 g (2.98 mmol) of bromotrimethylsilane. After stirring overnight at room temperature, the solvents are removed in vacuo and the crude product is dissolved in 10 ml of 50% aqueous THF, then heated with 2 ml of 2 N aq. NaOH at room temperature for 16 hours. The reaction mixture is neutralized with aqueous HCl and concentrated in vacuo. The residue is finally purified by chromatography on a Sephadex LH-20 gel filtration column to afford the title product.

EXAMPLE 9

(±)-1-[5-(1H-Imidazol-2-yl)-2-[hydroxy(4-phenylbutyl)phosphinyl]-1-oxopentyl]-L-proline A. 3-(1-t-Butyloxycarbonylimidazol-2-yl)-1-iodopropane In the manner as described in Example 6, parts A, B and C, except using 3-(1H-imidazol-2-yl)propane-1-ol instead of 3-(1H-imidazol-4-yl)propane-1-ol in part A, the title A compound is obtained.

B. (±)-1-[5-(1H-Imidazol-2-yl)-2-[hydroxy(4-phenylbutyl)phosphinyl]-1-oxopentyl]-L-proline In the manner described for the preparation of the Example 8 compound from 3-(1H-imidazol-4-yl)-1-iodopropane and by using 3-(1-t-butyloxycarbonylimidazol-2-yl)-1-iodopropane, in place 3-(1H-imidazol-4-yl)-1-iodopropane, the title product is prepared.

EXAMPLE 10

(±)-1-[5-Formylamino-2-[hydroxy-(4-phenylbutyl)phosphinyl]-1-oxopentyl]-L-proline A solution of 1 g (2.44 mmol) of (±)-1-[5-amino-2-[hydroxy-(4-phenylbutyl)phosphinyl]-1-oxopentyl]-L-proline (prepared as described in Example 1) in a mixture of 5 ml of acetic anhydride and 15 ml of 90% formic acid is kept at room temperature for 3 hours, then evaporated to give the title product.

EXAMPLE 11

(±)-1-[6-Formylamino-2-[[hydroxy(4-phenylbutyl)-]methyl]-1-oxohexyl]-L-proline

A solution of 1 g (2.22 mmol) of (±)-1-[6-amino-2-[[hydroxy(4-phenylbutyl)phosphinyl]methyl]-1-oxohexyl]-L-proline, dilithium salt (prepared as described in Example 2) in a mixture of 5 ml of acetic anhydride and 15 ml of 90% formic acid is kept at room temperature for 3 hours, then evaporated to give the title product.

EXAMPLE 12

(±)-1-[6-Amino-2-[[[(2,2-dimethyl-1-oxopropoxy)methoxy](4-phenylbutyl)phosphinyl]methyl]hexyl]-L-proline, (2,2-dimethyl-1-oxopropoxy)methyl ester, 4-methylbenzenesulfonic acid (1:1) salt A. (±)-1-[6-Phenylmethoxycarbonylamino-2-[[hydroxy(4-phenylbutyl)phosphinyl]methyl]-1-oxohexyl]-L-proline, (2,2-dimethyl-1-oxopropoxy)methyl ester To a solution of 1 g (2.10 mmol) of the diacid (prepared as described in Example 2, part G, in 7 ml of dry THF cooled in an ice-water bath under argon was added 358 mg (2.21 mmol) of carbonyldiimidazole. After 1 hour, the cold reaction mixture was treated with 852 mg (2.10 mmol) of L-proline, pivaloyloxymethyl ester, p-toluenesulfonic acid salt followed by 452 mg (4.20 mmol) of triethylamine. The reaction mixture was allowed to come to room temperature overnight, then diluted with ethyl acetate and rinsed with 10% KHSO$_4$, H$_2$O and brine. The organic extract was dried (MgSO$_4$) and concentrated in vacuo to yield 1.44 g of crude product. Flash chromatography on 60 g of LPS-1 silica gel eluted with 30:1:1, CH$_2$CH$_2$:MeOH:HOAc yielded 976 mg (68%) of the title A compound as an oil: $[\alpha]_D = -15.8$ (c=1, CHCl$_3$); TLC R$_f$=0.12 in 30:1:1, CH$_2$Cl$_2$:MeOH:HOAc (UV, PMA).

B. (±)-1-[6-Phenylmethoxycarbonylamino-2-[[[2,2-dimethyl-1-oxopropoxy)-methoxy](4-phenylbutyl)-phosphinyl]methyl]hexyl]-L-proline, (2,2-dimethyl-1-oxopropoxy)methyl ester To a mixture of 950 mg (1.38 mmol) of title A compound and 625 mg (4.15 mmol) of chloromethylpivalate (Aldrich) in 1.5 ml of dry DMF was added 75 mg of sodium iodide. After stirring 10 minutes, the reaction mixture was treated with 279 mg (2.76 mmol) of triethylamine. After stirring 1 day at room temperature under argon, the reaction mixture was diluted with 10 ml of ether and rinsed with portions of 10% KHSO$_4$, H$_2$O, and brine, then dried (MgSO$_4$) and concentrated in vacuo to 1.1 g of crude product. Flash chromatography on 44 g of LPS-1 silica gel eluted with 7:2:1, hexanes:ethyl acetate:methanol yielded 729 mg (66%) of title B compound as an oil: $[\alpha]_D = -33.1°$ (c=1, CHCl$_3$); TLC R$_f$=0.08 in 7:2:1, hexanes:ethyl acetate:methanol (UV, PMA).

C. (±)-1-[6-Amino-2-[[[(2,2-dimethyl-1-oxopropoxy)methoxy](4-phenylbutyl)phosphinyl]methyl]hexyl]-L-proline, (2,2-dimethyl-1-oxopropoxy)methyl ester, 4-methylbenzenesulfonic acid (1:1) salt A solution of 402 mg (0.502 mmol) of title B compound and 114 mg (0.602 mmol) of p-toluene-sulfonic acid, monohydrate in 15 ml of methanol was subjected to a steady flow of H$_2$ at 1 atm in the presence of 150 mg of 10% Pd-C. After 3 hours, the reaction mixture was filtered and concentrated in vacuo to an oil which was purified by reverse phase gradient elution chromatography on a 25×250 mm HP-20 Diaion ® reverse phase column eluted from 100% H$_2$O (500 ml) to 100% CH$_3$CN (500 ml) at a flow rate of ca. 4 ml/min with collection at 2 min/fraction. Fractions 51–57 yielded ca. 40 mg of mono-POM ester product, while pooling and lyophilizing of fractions 59–69 yielded 286 mg of product as an oil. This material was dissolved in 30 ml of ether and distributed into vials for characterization and testing. Evaporation of the ether gave the title product, an oil, as a 0.5 H$_2$O solvate (261 mg, 61% yield).

EXAMPLE 13

(±)-1-[6-Amino-2-[[hydroxy(4-phenylbutyl)phosphinyl]methyl]-1-oxohexyl]-L-proline, (2,2-dimethyl-1-oxopropoxy)methyl ester A solution of 0.800 g (1.16 mmol) of (±)-1-[6-amino-2-[[[(2,2-dimethyl-1-oxopropoxy)methoxy](4-phenylbutyl)phosphinyl]methyl]hexyl]-L-proline, (2,2-dimethyl-1-oxopropoxy)methyl ester, 4-methylbenzenesulfonic acid (1:1) salt (prepared as described in Example 12) in a mixture of 15 ml of methanol and 1 ml of acetic acid was cooled in an ice-water bath under argon and treated with 250 mg of 10% Pd-C. The reaction mixture was subjected to a slow flow of H$_2$ at 1 atm for 3½ hours, then filtered and concentrated in vacuo to 0.710 g of residue which was purified by reverse phase gradient elution chromatography on a 25×250 mm HP-20 column (500 ml H$_2$O to 500 ml CH$_3$CN, linear gradient at ca. 4 ml/min flow). The product containing fractions were pooled and lyophilized to yield 0.476 g (75%) of the title product isolated as a 0.9 H$_2$O solvate.

EXAMPLE 14

(±)-1-[6-Amino-2-[[hydroxy(2-phenylethyl)phosphinyl]methyl]-1-oxohexyl]-L-proline, dilithium salt A. 2-Phenylethylphosphonous acid, diethyl ester A suspension of 4.13 g (0.172 mol) of magnesium in 45 ml of dry ether under argon was treated with a solution of 31.2 g (0.168 mol) of 1-bromo-2-phenylethane (Aldrich) in 90 ml of dry ether, added at a rate that maintained reflux. The reaction was stirred overnight at room temperature under argon, then filtered under argon, cooled to 10° C. and treated with 26.3 g (0.168 mol) of diethyl chlorophosphonite (Aldrich) dissolved in 60 ml of dry ether, added slowly to keep the temperature near 10° C. After addition, the reaction was refluxed for 1 hour, filtered under argon and distilled at 1 atm to remove ether. Vacuum distillation of the residue gave 20.6 g (54%) of the title A compound which distilled at 94°–96° C./0.55 mm Hg. The $^1$H-NMR and $^{13}$C-NMR of this material were both consistent with the assigned structure.

B. 6-Phthalimido-2-[[ethoxy(2-phenylethyl)phosphinyl]methyl]hexanoic acid, methyl ester A mixture of 2.33 g (8.11 mmol) of 2-methylidene-6-phthalimidohexanoic acid, methyl ester (prepared as described in Example 2, part D) and 2.02 g (8.92 mmol) of the title A compound in 0.8 ml of glacial acetic acid was heated under argon at 67°–70° C. for 27 hours. The reaction mixture was concentrated in vacuo to give 5.03 g of crude title B compound which was characterized by $^1$H-NMR and $^{13}$C-NMR spectroscopy and used without purification in the next step.

C. 6-Amino-2-[[hydroxy(2-phenylethyl)phosphinyl]methyl]hexanoic acid

A solution of 3.46 g (nom. 7.14 mmol) of the title B compound in a mixture of 8 ml of concentrated HCl, 8 ml of glacial acetic acid and 4 ml of H₂O was refluxed under N₂ for 48 hours, then cooled and diluted with 100 ml of H₂O and rinsed with three 40 ml portions of ether. The aqueous solution was concentrated in vacuo and applied to a 100 ml AC 50 W-X2 (H+) column. After elution with H₂O had returned to neutral pH, 2% aqueous pyridine was used to elute the desired product. Lyophilization afforded 2.70 g of crude title C compound as a white solid: TLC $R_f$=0.19 on silica gel in 7:2:1, i-Pr-OH:NH₃:H₂O (UV, PMA, NIN); electrophoresis at pH 2.5, 2000 V, 30 minutes, 5 mA gave −1.1 cm (NIN); satisfactory ¹H and ¹³C-NMR spectra were obtained on the title C compound as the di-Na+ salt. This material was used directly in the next reaction without further purification.

D. 6-Benzyloxycarbonylamino-2-[[hydroxy(2-phenylethyl)phosphinyl]methyl]hexanoic acid A suspension of 1.1 g (nom. 3.2 mmol) of the title C compound in 5 ml of dry acetonitrile at room temperature under nitrogen was treated with 3.3 g (12.8 mmol) of bis-trimethylsilyltrifluoroacetamide (Aldrich). After 90 minutes 0.818 g (4.8 mmol) of benzyloxychloroformate was added and the reaction was stirred at room temperature for 2 days, then quenched with 2 ml of H₂O, diluted with 100 ml of saturated NaHCO₃ solution and rinsed with ether. The aqueous solution was acidified with concentrated HCl to pH 1.2 and extracted with three 100 ml portions of 5:1, EtOAc:Et₂O. The combined organic extracts were rinsed with H₂O and brine, dried (MgSO₄) and concentrated in vacuo to 1.56 g of crude product: TLC $R_f$=0.40 on silica gel in 11:1:1, CH₂Cl₂:MeOH:HOAc (UV, PMA); electrophoresis at pH 6.5, 2000 V. 45 min, 15 mA was +4.4 cm (COOH spray); satisfactory ¹H and ¹³C-NMR, IR, and mass spectra were obtained for this intermediate. This product was used without further purification.

E. (±)-1-[6-Benzyloxycarbonylamino-2-[[hydroxy(2-phenylethyl)phosphinyl]methyl]-1-oxohexyl]-L-proline, benzyl ester A solution of 1.5 g (nom. 3.35 mmol) of title D compound in 12 ml of dry THF cooled in an ice-bath under N₂ was treated with 652 mg (4.02 mmol) of carbonyldiimidazole. After 1 hour, the reaction was treated with 810 mg (3.35 mmol) of L-proline, benzyl ester and 678 mg (6.7 mmol) of triethylamine. The reaction was allowed to warm to room temperature overnight, then partitioned between ether and 10% aqueous KHSO₄. The ether layer was rinsed with H₂O and brine, dried (MgSO₄) and concentrated in vacuo to afford 1.2 g of crude product. Flash chromatography on 50 g of LPS-1 Whatman silica gel eluted with 30:1:1, CH₂Cl₂:MeOH:HOAc afforded 700 mg (33%) of title E compound as an oil: TLC $R_f$=0.16 on silica gel in 20:1:1, CH₂Cl₂:MeOH:HOAc (UV, PMA); $[\alpha]_D$=−40.0° (c=1, MeOH); satisfactory ¹H and ¹³C-NMR, IR and mass spectra were obtained.

F. (±)-1-[6-Amino-2-[[hydroxy(2-phenylethyl)phosphinyl]methyl]-1-oxohexyl]-L-proline, dilithium salt A solution of 670 mg (1.05 mmol) of title E compound in 20 ml of MeOH was subjected to a steady flow of H₂ at 1 atm in the presence of 250 mg of 10% Pd/c. After 4 hours, the reaction mixture was filtered and concentrated in vacuo. The residue was converted to its di-Li+ salt and purified on a 25×250 mm HP-20 Diaion ® reverse phase column by gradient elution from 400 ml of 100% H₂O to 400 ml of 100% CH₃CN. Lyophilization afforded 240 mg (51%) of title product isolated as a 1.2 H₂O solvate.

EXAMPLES 15 TO 93

Following the procedure of Example 1 but employing the phosphonous diester shown in Col. I, the amine compound shown in Col. II, and the peptide shown in Col. III, the product shown in Col. IV is obtained. Both the $R_2$ and $R_4$ ester groups may be removed to yield the corresponding diacid or salt as set forth in Examples 2 and 3 or only the carboxylic ester group $R_4$ may be removed or only the $R_2$ ester group may be removed.

| Col. I | Col. II | Col. III | Col. IV |
|---|---|---|---|
| $R_1-\overset{O}{\underset{OR_2}{\overset{\|}{P}}}-CH_2-\overset{O}{\overset{\|}{C}}-OCH_3$ | $(C_6H_5)_3C-NH-(CH_2)_m-Br$ | $HX-OR_4$ | $R_1-\overset{O}{\underset{OR_2}{\overset{\|}{P}}}-\overset{NH_2}{\underset{}{\overset{\|}{CH}}}-(CH_2)_m-\overset{O}{\overset{\|}{C}}-X-OR_4$ |

| Ex. | $R_1$ | $R_2$ | m | $X-OR_4$ |
|---|---|---|---|---|
| 15. | H₃C—(CH₂)₅— | —CH₂—C₆H₅ | 0 | -N(pyrrolidine)-COOCH₂—C₆H₅ (L) |
| 16. | H₃C— | —C₂H₅ | 1 | -N(pyrrolidine)-COOCH₂—C₆H₅ (L) |
| 17. | C₆H₅— | —CH₂—C₆H₅ | 3 | -N(pyrrolidine)-COOCH₂—C₆H₅ (L) |

-continued
| | | | | |
|---|---|---|---|---|
| 18. | 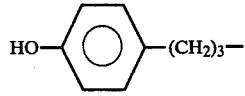 | —C$_2$H$_5$ | 5 | 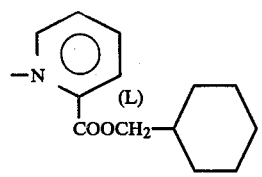 |
| 19. | 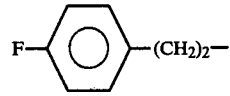 | —CH$_3$ | 2 | 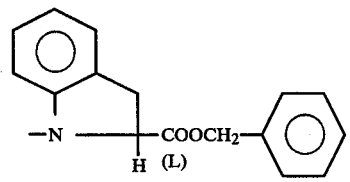 |
| 20. | 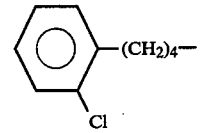 | 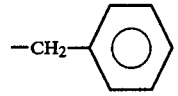 | 3 | 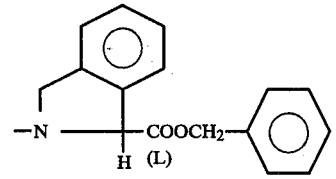 |
| 21. |  | —C$_2$H$_5$ | 4 | 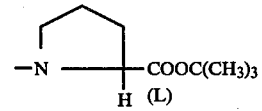 |
| 22. | 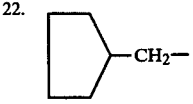 | —C$_2$H$_5$ | 0 | 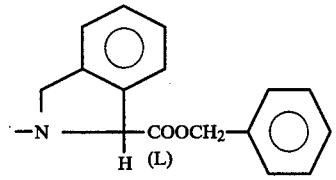 |
| 23. | 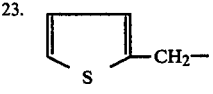 | —C$_2$H$_5$ | 1 | 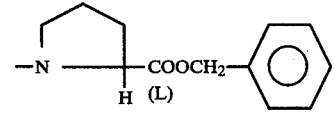 |
| 24. | 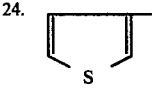 | 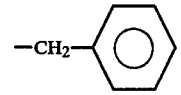 | 2 | 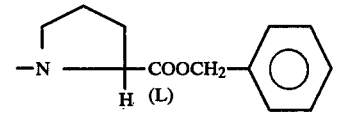 |
| 25. | 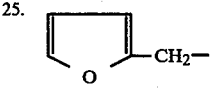 | 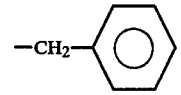 | 3 | 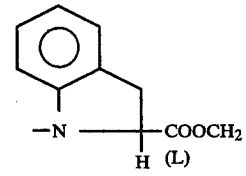 |
| 26. | 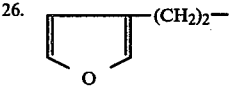 | —C$_2$H$_5$ | 4 | 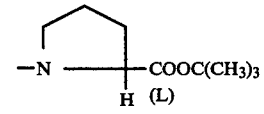 |

-continued
| | | | | |
|---|---|---|---|---|
| 27. | 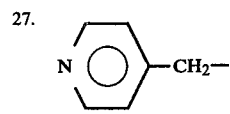 | —C$_2$H$_5$ | 5 | 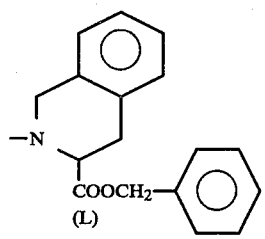 |
| 28. | 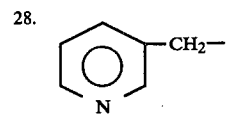 | 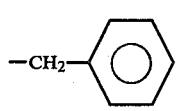—CH$_2$— | 0 | 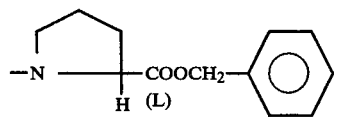 |
| 29. | H$_3$C—(CH$_2$)$_6$— | 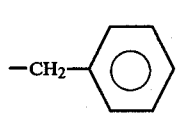—CH$_2$— | 1 | 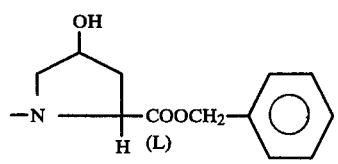 |
| 30. | H$_3$C—(CH$_2$)$_3$— | —C$_2$H$_5$ | 2 | 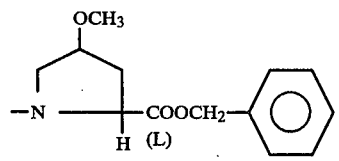 |
| 31. |  | —C$_2$H$_5$ | 3 | 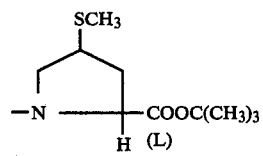 |
| 32. | 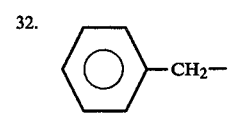 | —CH$_3$ | 4 | 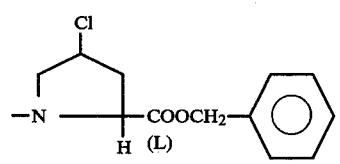 |
| 33. | 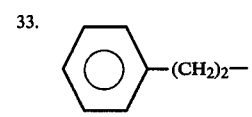 | 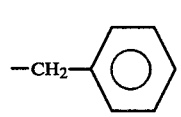—CH$_2$— | 5 | 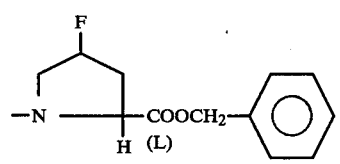 |
| 34. | 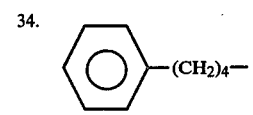 | —C$_2$H$_5$ | 0 | 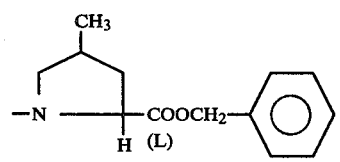 |
| 35. | 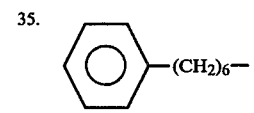 | 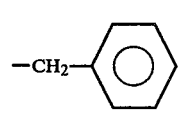—CH$_2$— | 1 | 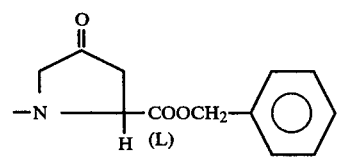 |

-continued
| | | | |
|---|---|---|---|
| 36. 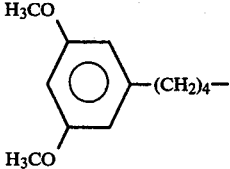 | 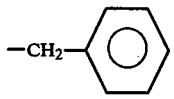 | 2 | 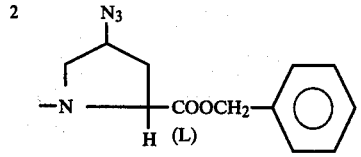 |
| 37. 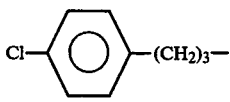 | 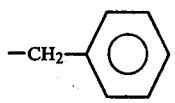 | 3 | 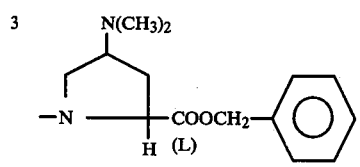 |
| 38. 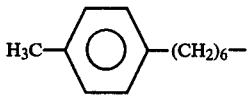 | 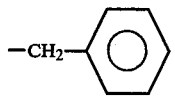 | 4 | 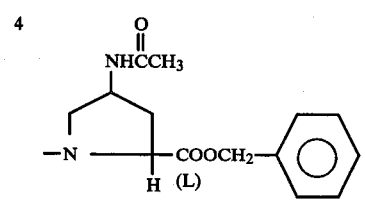 |
| 39. 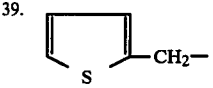 | —C$_2$H$_5$ | 5 | 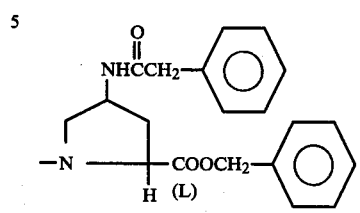 |
| 40. 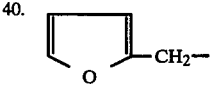 | —C$_2$H$_5$ | 0 | 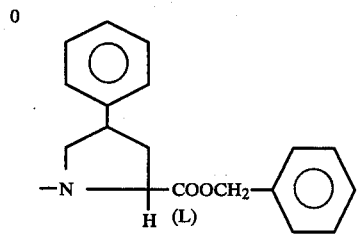 |
| 41. 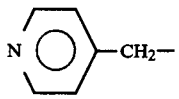 | —C$_2$H$_5$ | 1 | 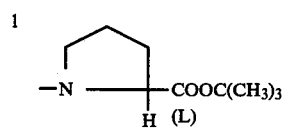 |
| 42. H$_5$C$_2$— | 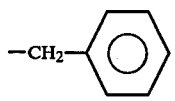 | 4 | 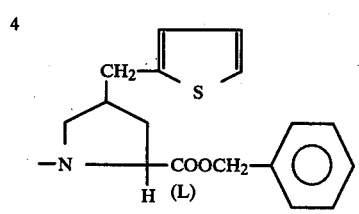 |
| 43. 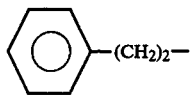 | 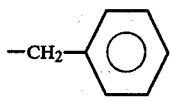 | 5 | 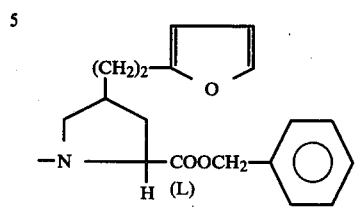 |

-continued
| 44. | 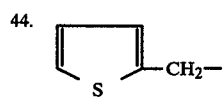 | 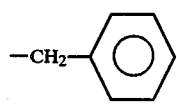 | 0 | 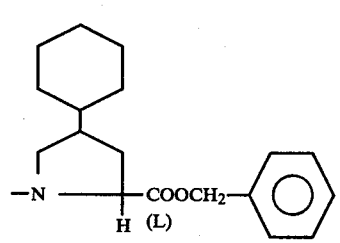 |
| 45. | 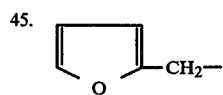 | 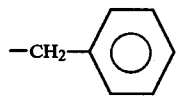 | 1 | 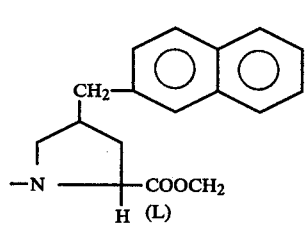 |
| 46. | 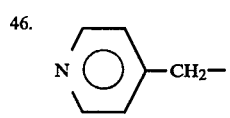 | 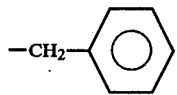 | 2 | 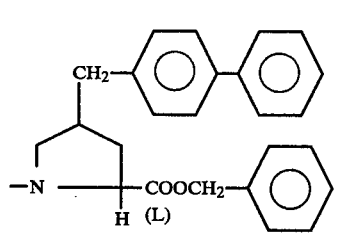 |
| 47. | $H_3C-(CH_2)_5-$ | 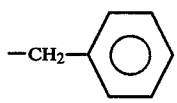 | 3 | 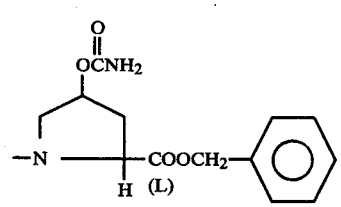 |
| 48. | 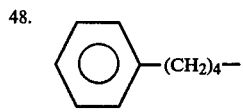 | 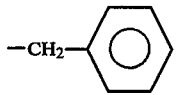 | 4 | 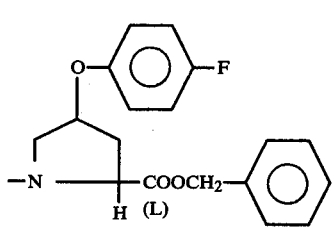 |
| 49. |  | 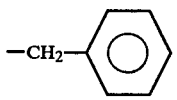 | 5 | 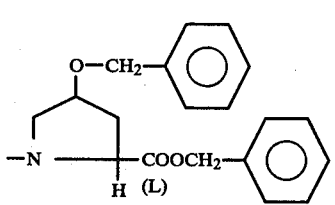 |
| 50. | 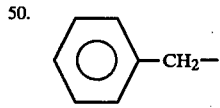 | $-C_2H_5$ | 0 | 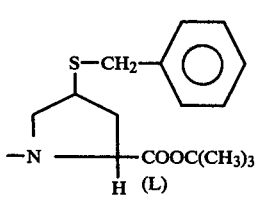 |

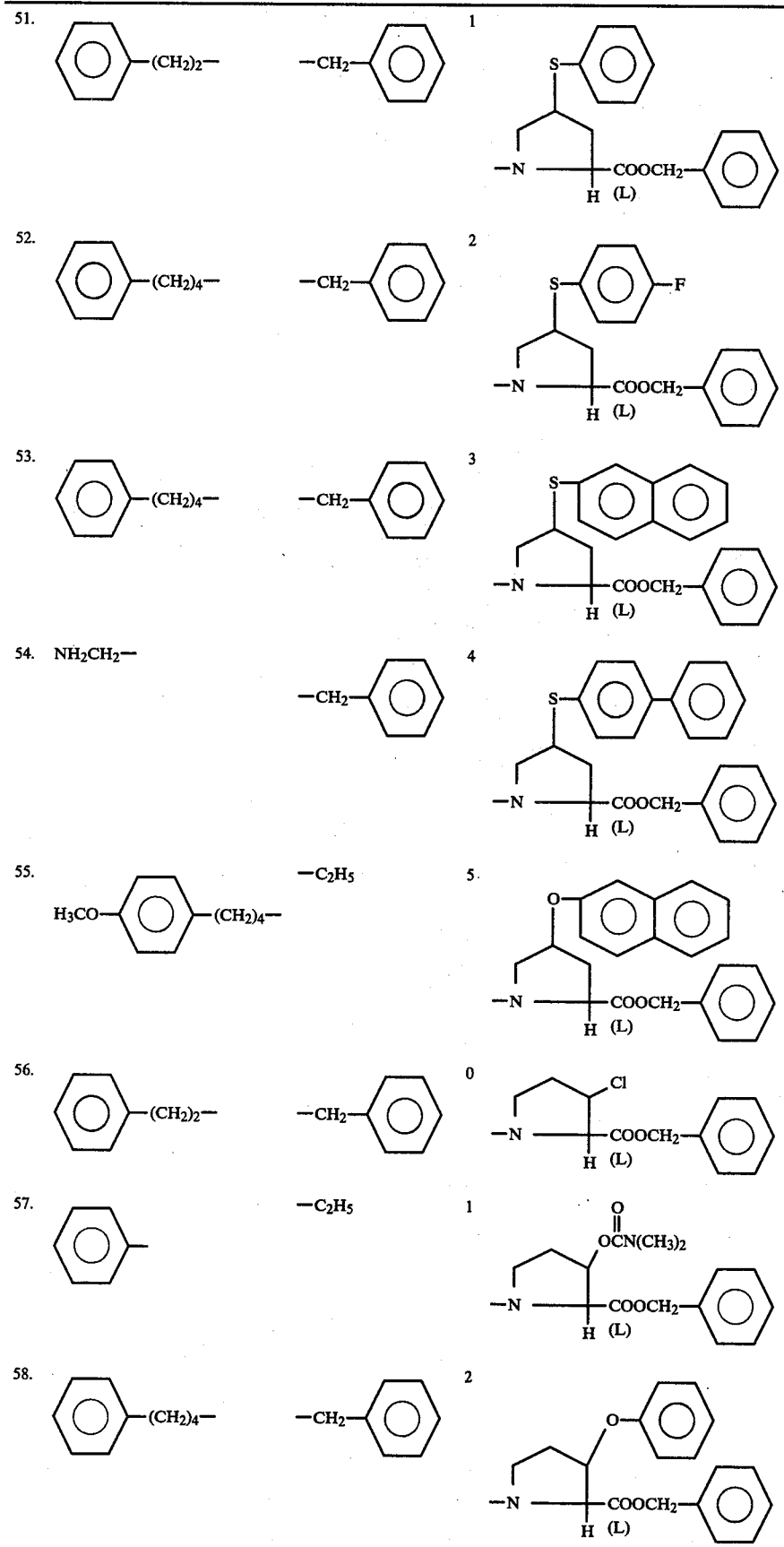

-continued
| | | | | |
|---|---|---|---|---|
| 59. | NH$_2$(CH$_2$)$_2$— | —CH$_2$—Ph | 3 | 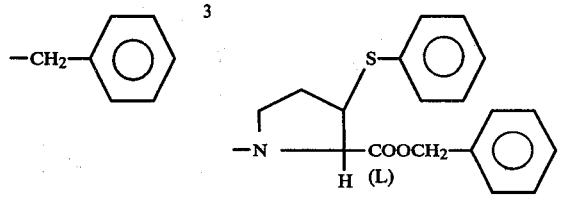 |
| 60. | Ph—(CH$_2$)$_5$— | —CH$_2$—Ph | 4 | 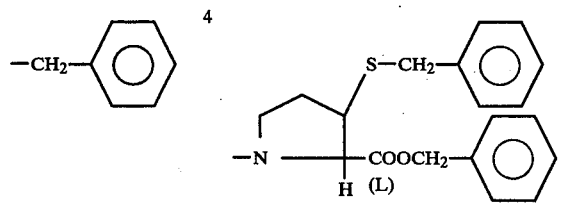 |
| 61. | H$_3$C—(CH$_2$)$_3$— | —CH$_2$—Ph | 5 | 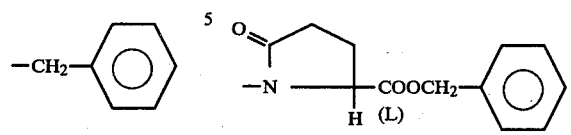 |
| 62. | Ph—(CH$_2$)$_4$— | —CH$_2$—Ph | 0 | 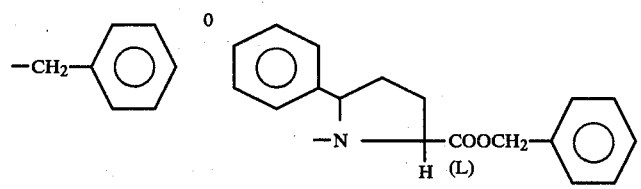 |
| 63. | Ph—(CH$_2$)$_2$— | —C$_2$H$_5$ | 1 | 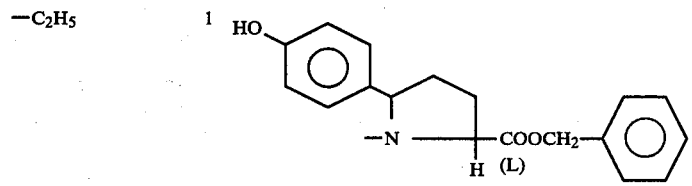 |
| 64. | thienyl-CH$_2$— | —CH$_2$—Ph | 2 | 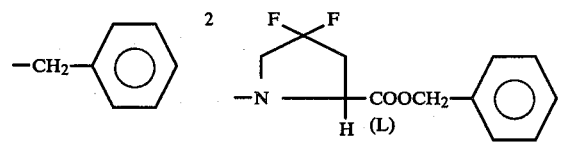 |
| 65. | furyl-CH$_2$— | —CH$_2$—Ph | 3 | 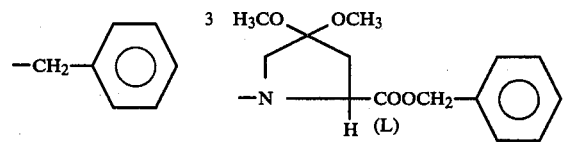 |
| 66. | Ph—(CH$_2$)$_4$— | —C$_2$H$_5$ | 4 | 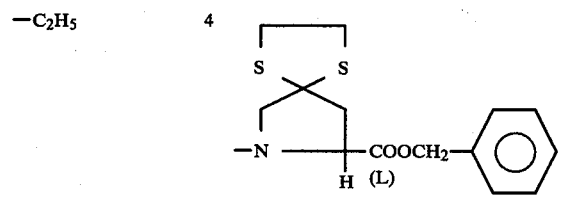 |
| 67. | Ph—(CH$_2$)$_2$— | —CH$_2$—Ph | 5 | 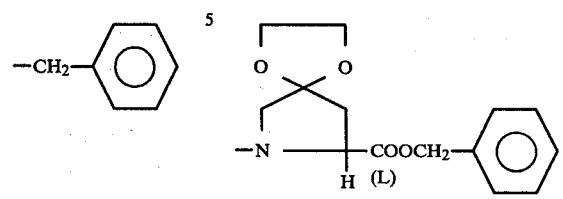 |

-continued
| | | | | |
|---|---|---|---|---|
| 68. |  | 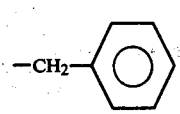 | 0 | 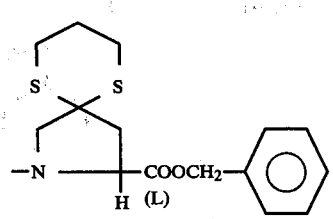 |
| 69. | 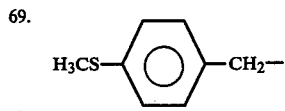 | 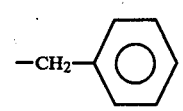 | 1 | 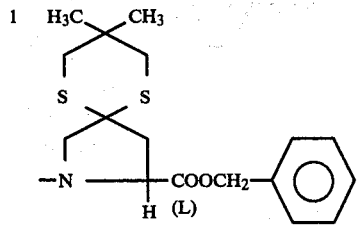 |
| 70. | NH$_2$(CH$_2$)$_2$— | —C$_3$H$_7$ | 2 | 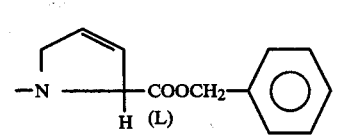 |
| 71. | 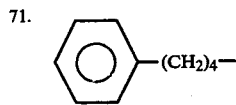 | 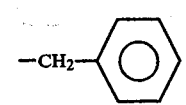 | 3 | 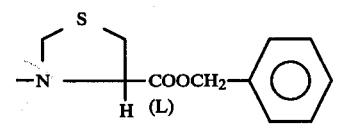 |
| 72. | 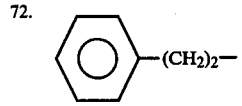 | —C$_2$H$_5$ | 4 | 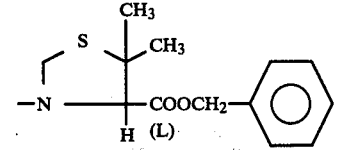 |
| 73. | H$_3$C—(CH$_2$)$_5$— | 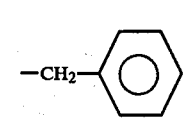 | 5 | 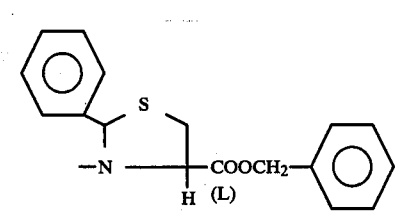 |
| 74. | 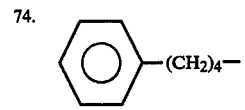 | 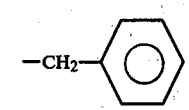 | 0 | 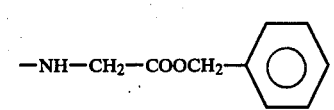 |
| 75. | 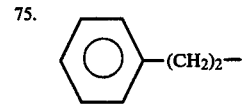 | 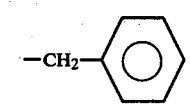 | 1 | 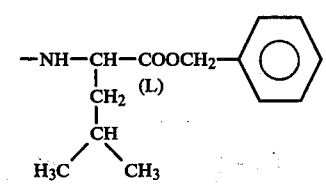 |
| 76. | 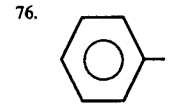 | 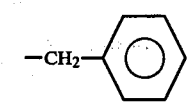 | 2 | 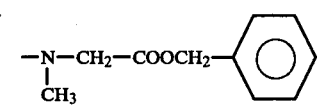 |

-continued
| | | | | |
|---|---|---|---|---|
| 77. | 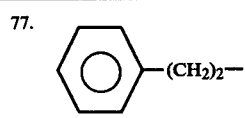 | —C$_2$H$_5$ | 3 | 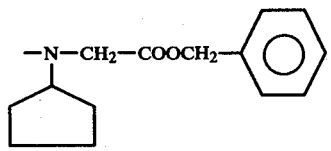 |
| 78. | 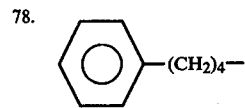 | 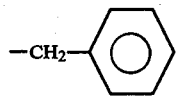 | 4 | 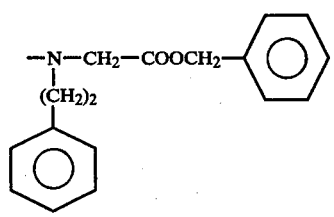 |
| 79. | H$_3$C—(CH$_2$)$_5$— | —C$_2$H$_5$ | 5 | 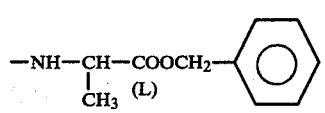 |
| 80. | 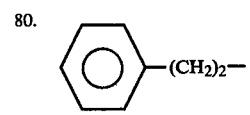 | 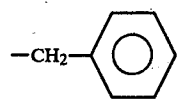 | 0 | 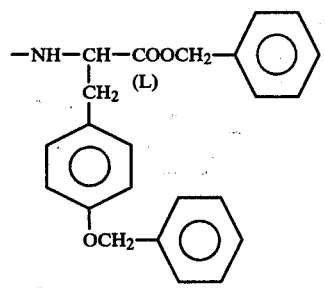 |
| 81. | NH$_2$CH$_2$— | 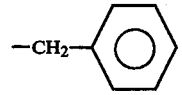 | 1 | 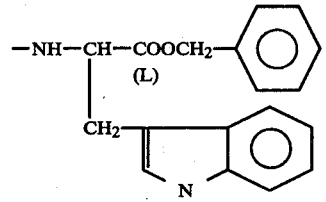 |
| 82. | 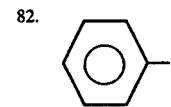 | 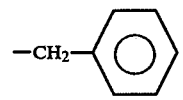 | 2 | 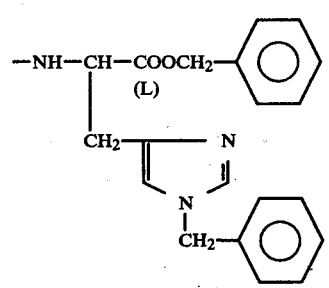 |
| 83. | 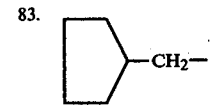 | 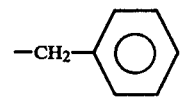 | 3 | 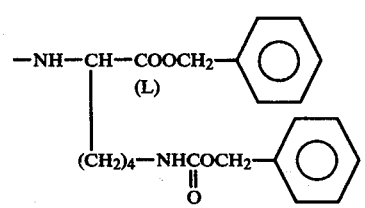 |

| | | | | |
|---|---|---|---|---|
| 84. | thiophene-CH₂— | —C₂H₅ | 4 | —NH—CH—COOCH₂—Ph (L) / CH₂—SCH₂—Ph |
| 85. | furan-CH₂— | —CH₂—Ph | 5 | —NH—CH—COOCH₂—Ph (L) / (CH₂)₂—S—CH₃ |
| 86. | Ph—(CH₂)₂— | —CH₂—Ph | 0 | —NH—CH—COOCH₂—Ph (L) / (CH₂)₃—NHC(=NH)NH—NO₂ |
| 87. | Ph—(CH₂)₄— | —C₂H₅ | 1 | —NH—CH—COOCH₂—Ph / CH₂—C(=O)—NH₂ |
| 88. | Ph—(CH₂)₄— | —CH₂—Ph | 5 | proline —N(H)—CH—C(=O)—O—CH₂—C(=O)—C(CH₃)₃ (L) |
| 89. | Ph—(CH₂)₂— | —CH₂—Ph | 0 | dithiolane-proline —N(H)—CH—C(=O)—O—CH(CH₃)—C(=O)—CH₃ (L) |
| 90. | H₃C—(CH₂)₅— | —CH₂—Ph | 1 | proline —N(H)—CH—C(=O)—O—CH₂—C(=O)—Ph (L) |
| 91. | Ph—(CH₂)₂— | —CH₂—Ph | 2 | 4-(phenylthio)proline —N(H)—CH—C(=O)—O—CH₂—C(=O)—C(CH₃)₃ (L) |
| 92. | thiophene-CH₂— | —CH₂—Ph | 3 | 4-(naphthyloxy)proline —N(H)—CH—C(=O)—O—CH(CH₃)—C(=O)—C₂H₅ |

93. 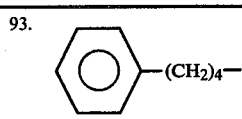 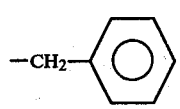 4 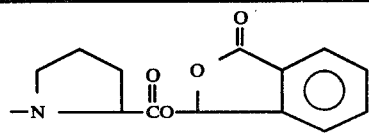

EXAMPLES 94 TO 172

Following the procedure of Examples 2 and 3, but employing the acrylate ester shown in Col. I (wherein m is as shown in Examples 15 to 93, respectively), the phosphonous compound shown in Col. II (wherein $R_1$ and $R_2$ are as shown in Examples 15 to 93, respectively), and the peptide shown in Col. III (wherein $X$—$OR_4$ are as shown in Examples 15 to 93, respectively), the product shown in Col. IV is obtained wherein $R_1$, $R_2$, m, X and $OR_4$ are as shown in Col. IV of Examples 15 to 93, respectively.

Both the $R_2$ and $R_4$ ester groups may be removed to yield the corresponding diacid or salt or only the carboxylic ester group $R_4$ may be removed or only the $R_2$ ester group may be removed.

Col. I $$CH_2=C\begin{matrix}(CH_2)_m-N=\text{protecting group}\\ COOCH_3\end{matrix}$$

Col. II $$R_1-P\begin{matrix}OR_2\\ OR_2\end{matrix}$$

(wherein $R_2$ is other than H)

HX—$OR_4$     Col. III

Col. IV

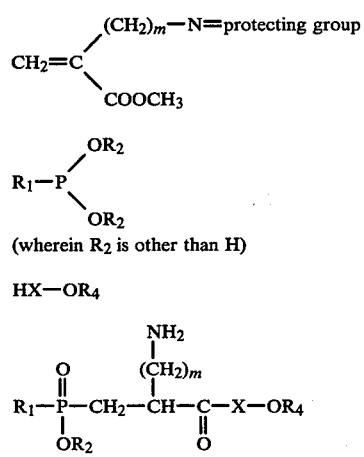

EXAMPLES 173 TO 261

Following the procedure of Example 4 but substituting for (±)-1-[6-amino-2-[[hydroxy-(4-phenylbutyl)-phosphinyl]methyl]-1-oxohexyl]-L-proline, dilithium salt, the Examples 1, 2, 3, 5 to 11 and Examples 15 to 172, and reacting each of such compounds with any of the acid anhydrides shown in Col. I, one obtains the corresponding product wherein $R_3$ is alkanoylamine

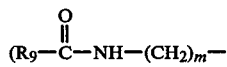

wherein $R_9$ is alkyl and m is 0 or 1 to 5), aralkanoylamine

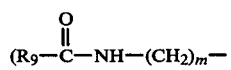

wherein $R_9$ is arylalkyl and m is 0 or 1 to 5) or aroylamine $$\underset{(R_9-\overset{O}{\overset{\|}{C}}-NH(CH_2)_m-)}{}$$

wherein $R_9$ is aryl, and m is 0 or 1 to 5).

| Col. I |
|---|
| $(R_9C)_2O$ |
| $R_9$ |
| $CH_3$ |
| $C_6H_5$ |
| $C_6H_5CH_2$ |
| $C_2H_5$ |
| $C_6H_5(CH_2)_2$ |
| $C_3H_7$ |

EXAMPLE 262

(±)-1-[6-Guanidion-2-[[hydroxy(4-phenylbutyl)phosphinyl]-1-oxopentyl]-L-proline

Following the procedure of Example 5 but employing as a starting material the Example 1 compound, the title compound is formed.

EXAMPLES 263 TO 420

Following the procedure of Example 5 but substituting as a starting material any of the Example 15 to 172 compounds, the corresponding guanidino compounds shown in Col. I below are obtained wherein $R_1$, $R_2$, n, m, X, and $OR_4$ are as shown in Examples 15 to 172.

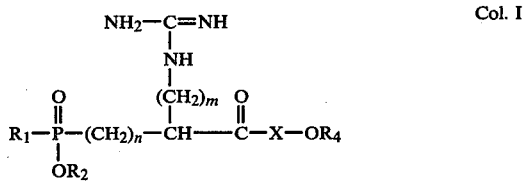

Col. I

EXAMPLES 421 TO 499

Following the procedure of Example 6 but employing the imidazole compound shown in Col. I (wherein m is as shown in Examples 15 to 93), the phosphinyl compound shown in Col. II (wherein $R_1$ and $R_2$ is as shown in Examples 15 to 93), and the peptide shown in Col. III (wherein X and $OR_4$ are as shown in Examples 15 to 93), the product shown in Col. IV is obtained (wherein $R_1$, $R_2$, m, X or $OR_4$ are shown in Col. IV of Examples 15 to 93, respectively).

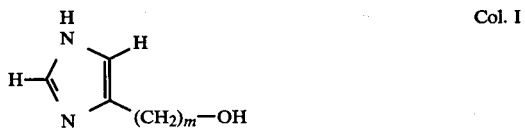

Col. I

-continued

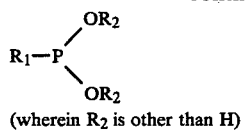
(wherein R₂ is other than H)

HX—OR₄  Col. III

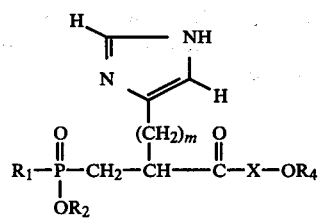
Col. IV.

EXAMPLES 500 TO 578

Following the procedure of Example 7 but employing the iodine compound shown in Col. I (wherein m is as shown in Examples 15 to 93), the phosphinyl compound shown in Col. II (wherein $R_1$ and $R_2$ is as shown in Examples 15 to 93) and the peptide shown in Col. III (wherein X and $OR_4$ are as shown in Examples 15 to 93), the product shown in Col. IV is obtained (wherein $R_1$, $R_2$, m, X and $OR_4$ are as shown in Examples 15 to 93, respectively).

Col. I

I—(CH₂)ₘ—O⟨tetrahydropyran⟩

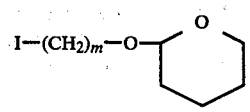
(wherein R₂ is other than H)

HX—OR₄  Col. III

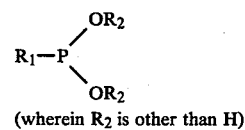  Col. IV

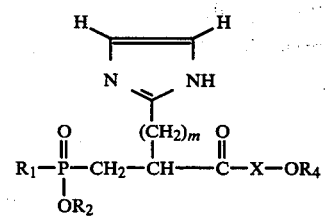

EXAMPLES 579 TO 657

Following the procedure of Example 8, but employing the imidazole compound shown in Col. I (wherein m is as shown in Examples 15 to 93, respectively), the phosphinyl compound shown in Col. II (wherein $R_1$ and $R_2$ are as shown in Examples 15 to 93, respectively) and the peptide shown in Col. III (wherein X—$OR_4$ is as shown in Examples 15 to 93, respectively), the product shown in Col. IV is obtained (wherein $R_1$, $R_2$, m, X and $OR_4$ are as shown in Col. IV of Examples 15 to 93, respectively).

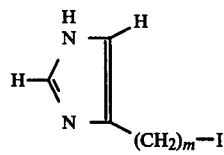  Col. I

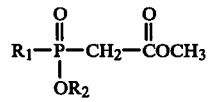  Col. II

HX—OR₄  Col. III

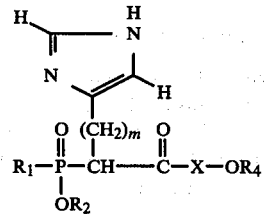  Col. IV

EXAMPLES 658 TO 736

Following the procedure of Example 9, but employing the imidazole compound shown in Col. I (wherein m is as shown in Examples 15 to 93, respectively), the phosphinyl compound shown in Col. II (wherein $R_1$ and $R_2$ are as shown in Examples 15 to 93, respectively), and the peptide shown in Col. III (wherein X—$OR_4$ is as shown in Examples 15 to 93, respectively), the product shown in Col. IV is obtained (wherein $R_1$, $R_2$, m, X and $OR_4$ are as shown in Col. IV of Examples 15 to 93, respectively).

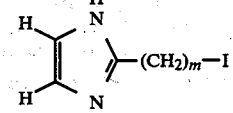  Col. I

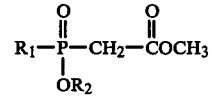  Col. II

HX—OR₄  Col. III

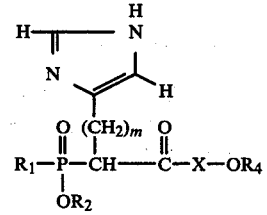  Col. IV

EXAMPLES 737 TO 815

Following the procedure of Example 10 except substituting for the Example 1 compound, the compound shown in Col. I (wherein $R_1$, $R_2$, m, X and $OR_4$ are as shown in Col. IV of Examples 15 to 93, respectively), the compound shown in Col. II is obtained.

Col. I

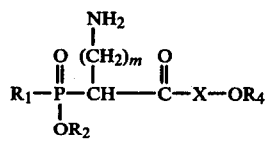

Col. II

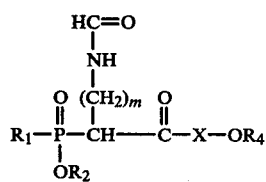

EXAMPLES 816 TO 894

Following the procedure of Example 11, except substituting for the Example 2 compound, the compound shown in Col. I (wherein $R_1$, $R_2$, m, X, and $OR_4$ are as shown in Col. IV of Examples 15 to 93, respectively), the compound shown in Col. II is obtained.

Col. I

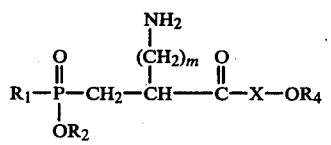

Col. II

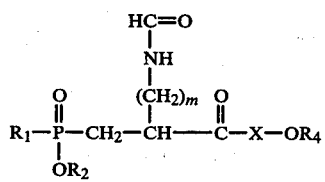

With respect to each of the compounds of Examples 173 to 894, both the $R_2$ and $R_4$ ester groups may be removed to yield the corresponding diacid or salt as shown in Examples 1 and 2 or only the carboxylic ester group $R_4$ may be removed or only the $R_2$ ester group may be removed.

What is claimed is:

1. A compound of the formula

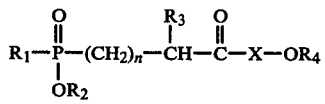

and pharmaceutically acceptable salts thereof, wherein $R_1$ is lower alkyl, aryl, arylalkyl, cycloalkyl, cycloalkylalkyl, aminoalkyl, furyl, furylalkyl, thienyl, thienylalkyl, pyridyl, pyridylalkyl or

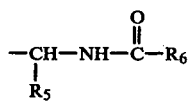

and $R_5$ and $R_6$ are independently selected from hydrogen, lower alkyl, haloalkyl, aryl, alkylaryl, cycloalkyl, cycloalkylalkyl furyl, furylalkyl, thienyl, thienylalkyl, pyridyl or pyridylalkyl;

$R_2$ and $R_4$ each is independently hydrogen, lower alkyl, arylalkyl, benzhydryl or

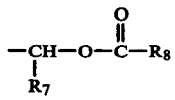

wherein $R_7$ is hydrogen, lower alkyl or phenyl, $R_8$ is hydrogen, lower alkyl, lower alkoxy or phenyl or $R_7$ and $R_8$ taken together are $-(CH_2)_2-$, $-(CH_2)_3-$, $-CH=CH-$, or

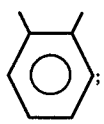

n is 0 or 1;
$R_3$ is $NH_2(CH_2)_m-$,

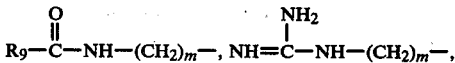

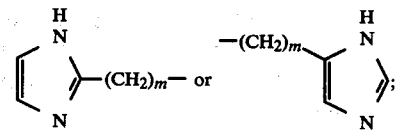

$R_9$ is hydrogen, lower alkyl, aryl or arylalkyl, and m is 0 or an integer of from 1 to 5, and $-XOR_4$ is an imino or amino acid derivative of the formula

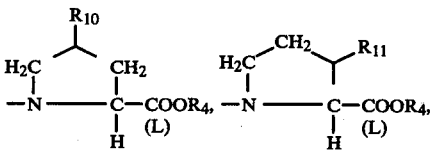

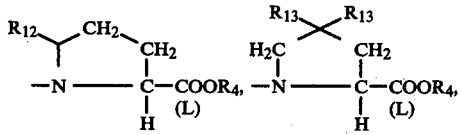

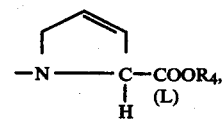

$R_{10}$ is hydrogen, lower alkyl, halogen, keto, hydroxy,

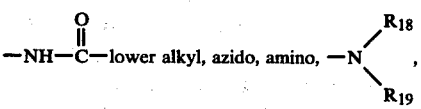

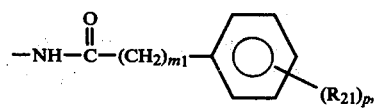

-continued

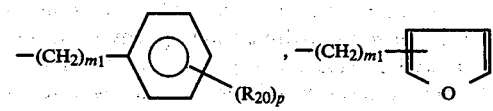

a 1- or 2-naphthyl of the formula

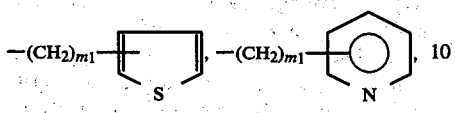

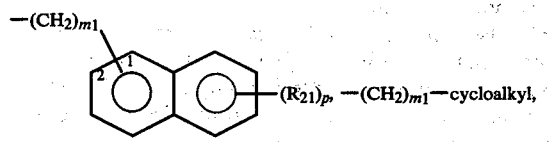

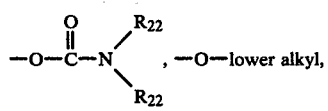

a 1- or 2-naphthyloxy of the formula

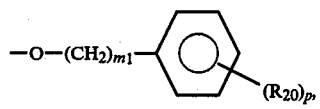

or a 1- or 2-naphthylthio of the formula

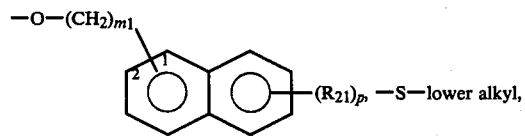

$R_{11}$ is keto, halogen,

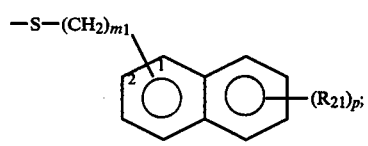

—O—lower alkyl, a 1- or 2-naphthyloxy of the formula

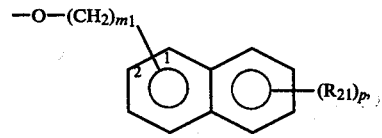

or a 1- or 2-naphthylthio of the formula

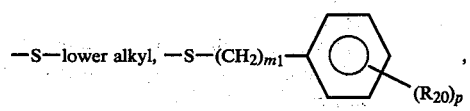

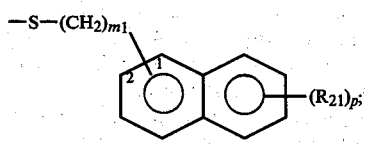

$R_{12}$ is keto or

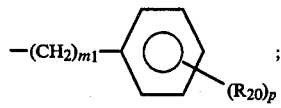

$R_{13}$ is halogen or —Y—$R_{23}$;

$R_{20}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_{21}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

$m_1$ is 0 or an integer from 1 to 5;

p is 1, 2 or 3 provided that p is more than 1 only if $R_{20}$ or $R_{21}$ is hydrogen, methyl, methoxy, chloro, or fluoro;

$R_{22}$ is hydrogen or lower alkyl of 1 to 4 carbons;

Y is oxygen or sulfur;

$R_{23}$ is lower alkyl of 1 to 4 carbons,

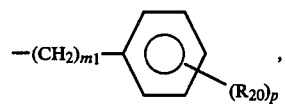

or the $R_{23}$ groups join to complete an unsubstituted 5- or 6-membered ring or said ring in which one or more of the carbons has a lower alkyl of 1 to 4 carbons or a di(lower alkyl of 1 to 4 carbons) substituent;

$R_{18}$ is lower alkyl, benzyl, or phenethyl; and $R_{19}$ is hydrogen, lower alkyl, benzyl or phenethyl.

2. The compound as defined in claim 1 wherein n is 0.

3. The compound as defined in claim 1 wherein n is 1.

4. The compound as defined in claim 1 wherein $R_3$ is $NH_2(CH_2)_m$ wherein m is 2 to 5.

5. The compound as defined in claim 1 wherein $R_1$ is arylalkyl.

6. The compound as defined in claim 1 wherein X—$OR_4$ is

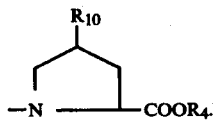

7. The compound as defined in claim 6 wherein $R_4$ is H or benzyloxy.

8. The compound as defined in claim 1 having the name (±)-1-[5-amino-2-[hydroxy-(4-phenylbutyl)phosphinyl]-1-oxopentyl]-L-proline.

9. The compound as defined in claim 1 having the name (±)-1-[6-amino-2-[[hydroxy(4-phenylbutyl)phosphinyl]methyl]-1-oxohexyl]-L-proline, benzyl ester.

10. The compound as defined in claim 1 having the name (±)-1-[6-amino-2-[[hydroxy (4-phenylbutyl)phosphinyl]methyl]-1-oxohexyl]-L-proline, dilithium salt.

11. The compound as defined in claim 1 having the name (±)-1-[6-acetylamino-2-[[[hydroxy(4-phenylbutyl)phosphinyl]methyl]-1-oxohexyl]-L-proline.

12. The compound as defined in claim 1 having the name (±)-1-[6-amino-2-[[hydroxy(4-phenylbutyl)phosphinyl]methyl]-1-oxohexyl]-L-proline, (2,2-dimethyl-1-oxopropoxy)methyl ester.

13. The compound as defined in claim 1 having the name (±)-1-[6-amino-2-[[hydroxy(2-phenylethyl)phosphinyl]methyl]-1-oxohexyl]-L-proline, dilithium salt.

14. A composition useful for treating hypertension comprising a pharmaceutically acceptable carrier and a hypotensive agent as defined in claim 1 or pharmaceutically acceptable salt thereof.

15. The method of alleviating hypertension in a mammalian specie which comprises administering an effective amount of the composition of claim 14.

16. The compound as defined in claim 1 having the name (±)-1-[6-amino-2-[[[(2,2-dimethyl-1-oxopropoxy)methoxy](4-phenylbutyl)phosphinyl]methyl]-1-oxohexyl]-L-proline.

17. The compound as defined in claim 1 having the name (±)-1-[6-amino-2-[[[(2,2-dimethyl-1-oxopropoxy)methoxy](4-phenylbutyl)phosphinyl]methyl]hexyl]-L-proline, (2,2-dimethyl-1-oxopropoxy)methyl ester, 4-methylbenzenesulfonic acid (1:1) salt.

* * * * *

UNITED STATES PATENT AND TRADEMARK OFFICE
CERTIFICATE OF CORRECTION

PATENT NO. : 4,452,791
DATED : June 5, 1984
INVENTOR(S) : Denis Ryono, et al.

It is certified that error appears in the above—identified patent and that said Letters Patent is hereby corrected as shown below:

Column 1, line, 53, "and" should read --are--.
Column 2, line 60, "amino" should read --imino--.
Column 27, line 60, delete "B".
Example 41, the structure in Col. IV should read

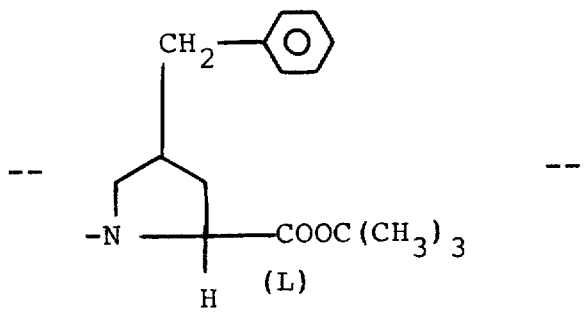

Signed and Sealed this

First Day of January 1985

[SEAL]

Attest:

Attesting Officer

GERALD J. MOSSINGHOFF

Commissioner of Patents and Trademarks